United States Patent
Xu

(10) Patent No.: US 11,774,445 B2
(45) Date of Patent: Oct. 3, 2023

(54) PARTICLE TRAPPING DEVICE AND PARTICLE TRAPPING METHOD

(71) Applicant: University Public Corporation Osaka, Osaka (JP)

(72) Inventor: Yan Xu, Sakai (JP)

(73) Assignee: UNIVERSITY PUBLIC CORPORATION OSAKA, Osaka (JP)

(*) Notice: Subject to any disclaimer, the term of this patent is extended or adjusted under 35 U.S.C. 154(b) by 831 days.

(21) Appl. No.: 16/614,112

(22) PCT Filed: May 17, 2018

(86) PCT No.: PCT/JP2018/019203
§ 371 (c)(1),
(2) Date: Nov. 15, 2019

(87) PCT Pub. No.: WO2018/212309
PCT Pub. Date: Nov. 22, 2018

(65) Prior Publication Data
US 2020/0173987 A1 Jun. 4, 2020

(30) Foreign Application Priority Data

May 17, 2017 (JP) ................................. 2017-098247

(51) Int. Cl.
*B01L 3/00* (2006.01)
*G01N 33/543* (2006.01)
(Continued)

(52) U.S. Cl.
CPC .......... *G01N 33/54346* (2013.01); *B01L 3/502761* (2013.01); *C12M 1/34* (2013.01);
(Continued)

(58) Field of Classification Search
None
See application file for complete search history.

(56) References Cited

U.S. PATENT DOCUMENTS

2002/0108889 A1 8/2002 Fujii et al.
2008/0302732 A1 12/2008 Soh et al.
(Continued)

FOREIGN PATENT DOCUMENTS

EP 2150350 * 4/2012
JP 2002-233792 A 8/2002
(Continued)

OTHER PUBLICATIONS

Xu, Yan, et al. "Site-specific nanopatterning of functional metallic and molecular arbitrary features in nanofluidic channels." Lab Chip, 2015, 15, 1989-1993.

*Primary Examiner* — Rebecca M Giere
(74) *Attorney, Agent, or Firm* — Stites & Harbison, PLLC; Jeffrey A. Haeberlin; Patrick M. Torre

(57) ABSTRACT

The particle trapping device according to the present invention comprises: a lead-in channel; a flattened channel disposed on the downstream side of the lead-in channel; a rectangular channel disposed on the downstream side of the flattened channel; and a particle pit trap disposed at least on a first inner wall face of the rectangular channel, wherein the lead-in channel has a channel cross-section larger than a channel cross-section of the flattened channel; the flattened channel has a flat channel cross-section whose the width is longer than its height; the rectangular channel has a rectangular channel cross-section, and is provided with the first inner wall face, a second inner wall face opposed to the first inner wall face, a third inner wall face, and a fourth inner wall face opposed to the third inner wall face; and the lead-in channel, the flattened channel, the rectangular channel, and the particle pit trap are characterized by being configured in such a way that a portion of liquid containing target particles and flowing through the lead-in channel flows into the flattened channel; the target particles contained in the liquid that had flowed through the flattened channel flow into the (Continued)

rectangular channel; and the target particle that had flowed through the rectangular channel enters into the particle pit trap and is trapped therein.

16 Claims, 12 Drawing Sheets

(51) Int. Cl.
  *G01N 33/536* (2006.01)
  *C12M 1/34* (2006.01)
  *G01N 15/14* (2006.01)
  *G01N 1/10* (2006.01)
  *G01N 15/00* (2006.01)

(52) U.S. Cl.
  CPC ....... *G01N 15/1484* (2013.01); *G01N 33/536* (2013.01); *B01L 2200/0668* (2013.01); *B01L 2300/0864* (2013.01); *B01L 2300/0896* (2013.01); *G01N 1/10* (2013.01); *G01N 2015/0038* (2013.01); *G01N 2015/0065* (2013.01)

(56) References Cited

U.S. PATENT DOCUMENTS

| | | | |
|---|---|---|---|
| 2009/0214392 A1* | 8/2009 | Kameoka | B01L 3/502761 156/60 |
| 2011/0027854 A1 | 2/2011 | Suda et al. | |
| 2014/0329722 A1* | 11/2014 | Perroud | B81C 1/00404 435/174 |
| 2018/0180604 A1 | 6/2018 | Itonaga et al. | |

FOREIGN PATENT DOCUMENTS

| | | |
|---|---|---|
| JP | 2011-045358 A | 3/2011 |
| JP | 2017-040595 A | 2/2017 |

* cited by examiner

[FIG. 1]
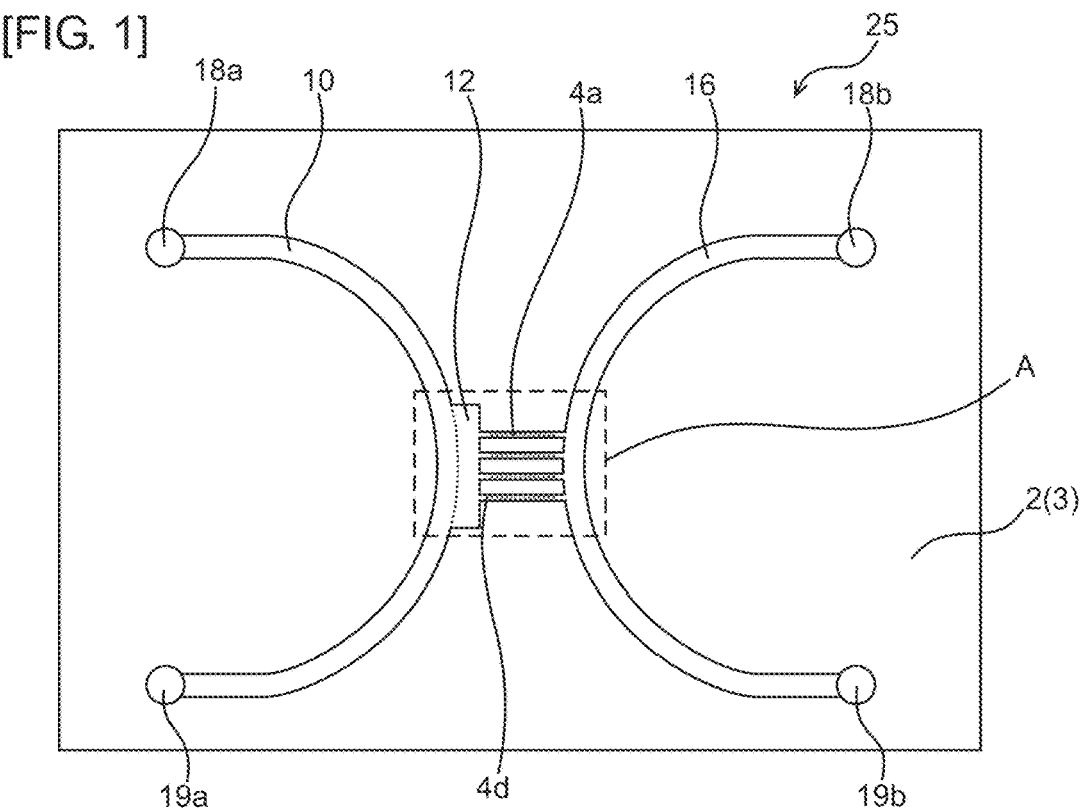
[FIG. 2]
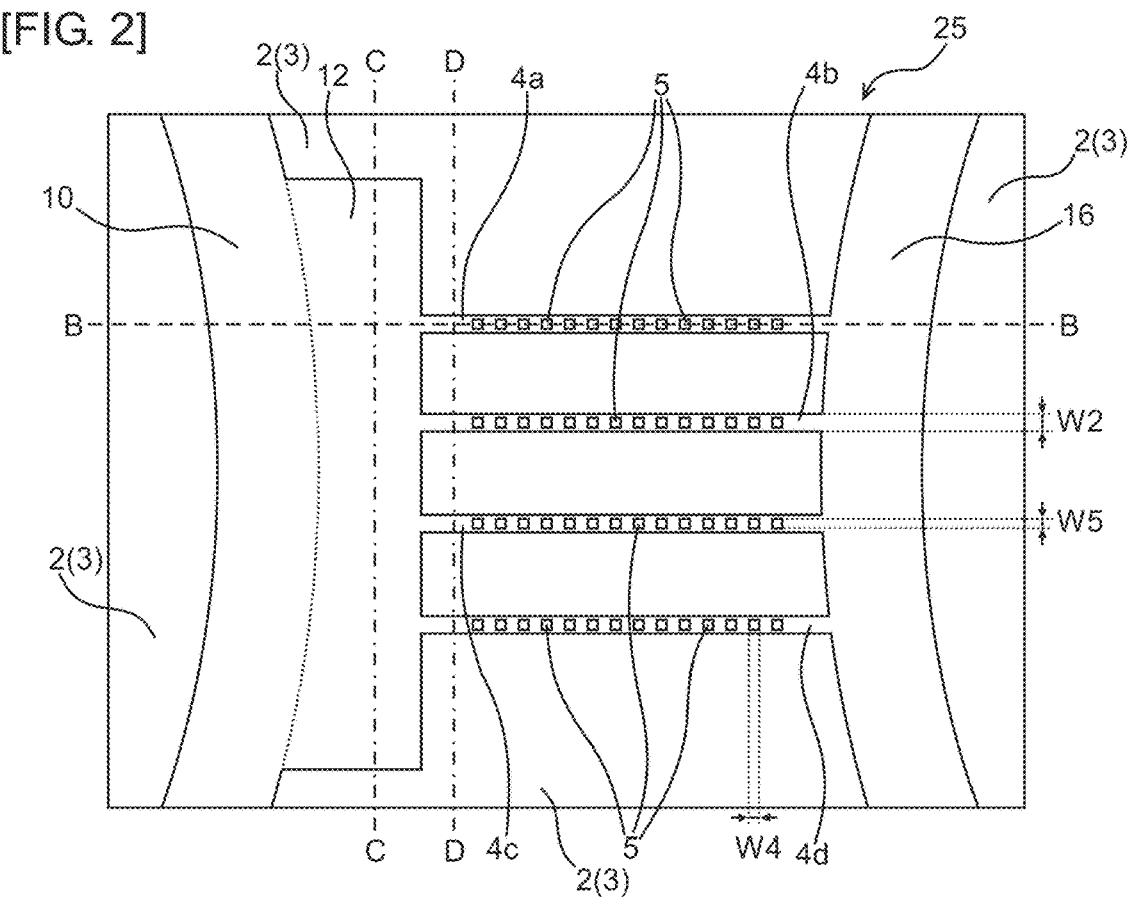

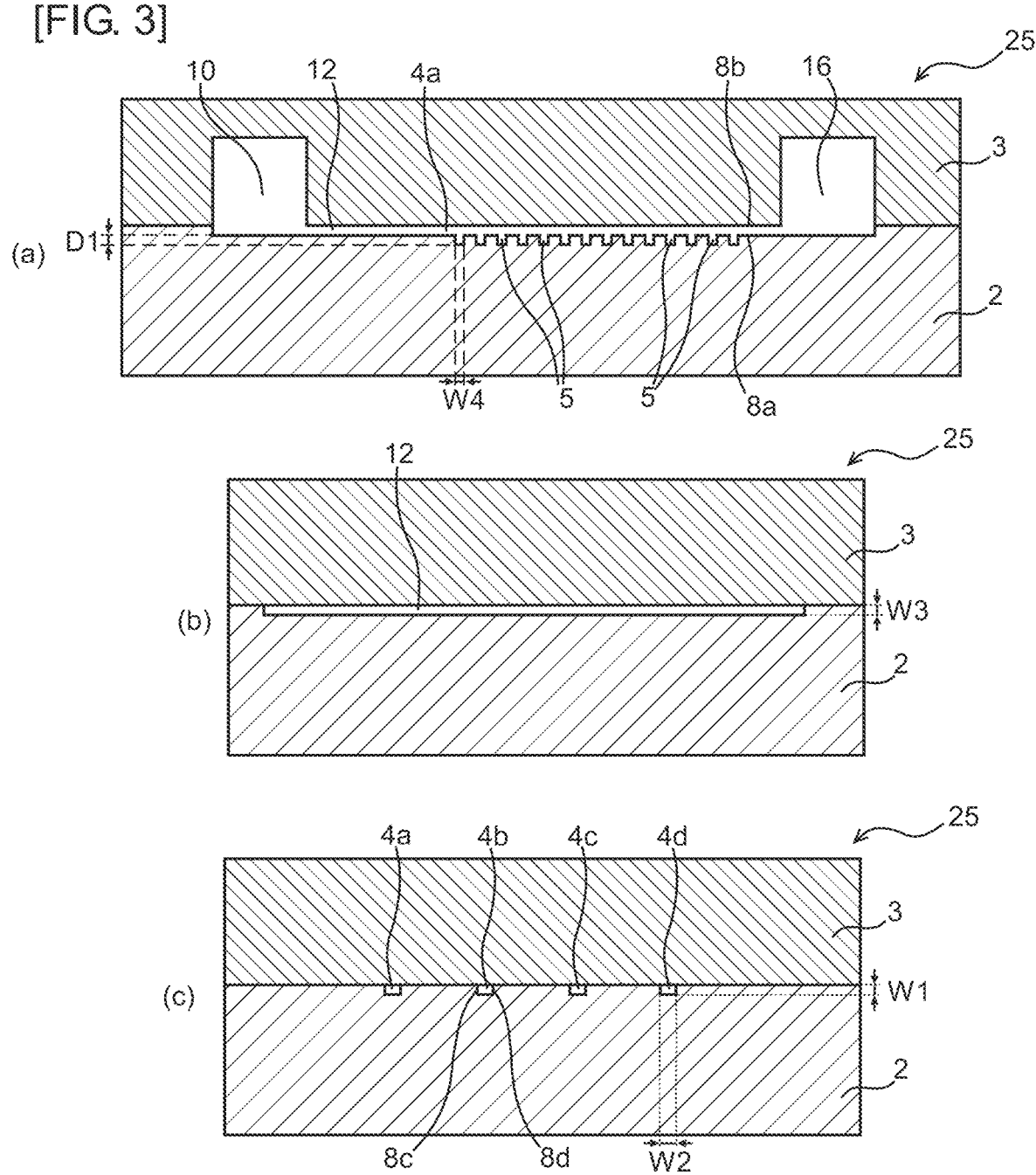
[FIG. 3]

[FIG. 4]
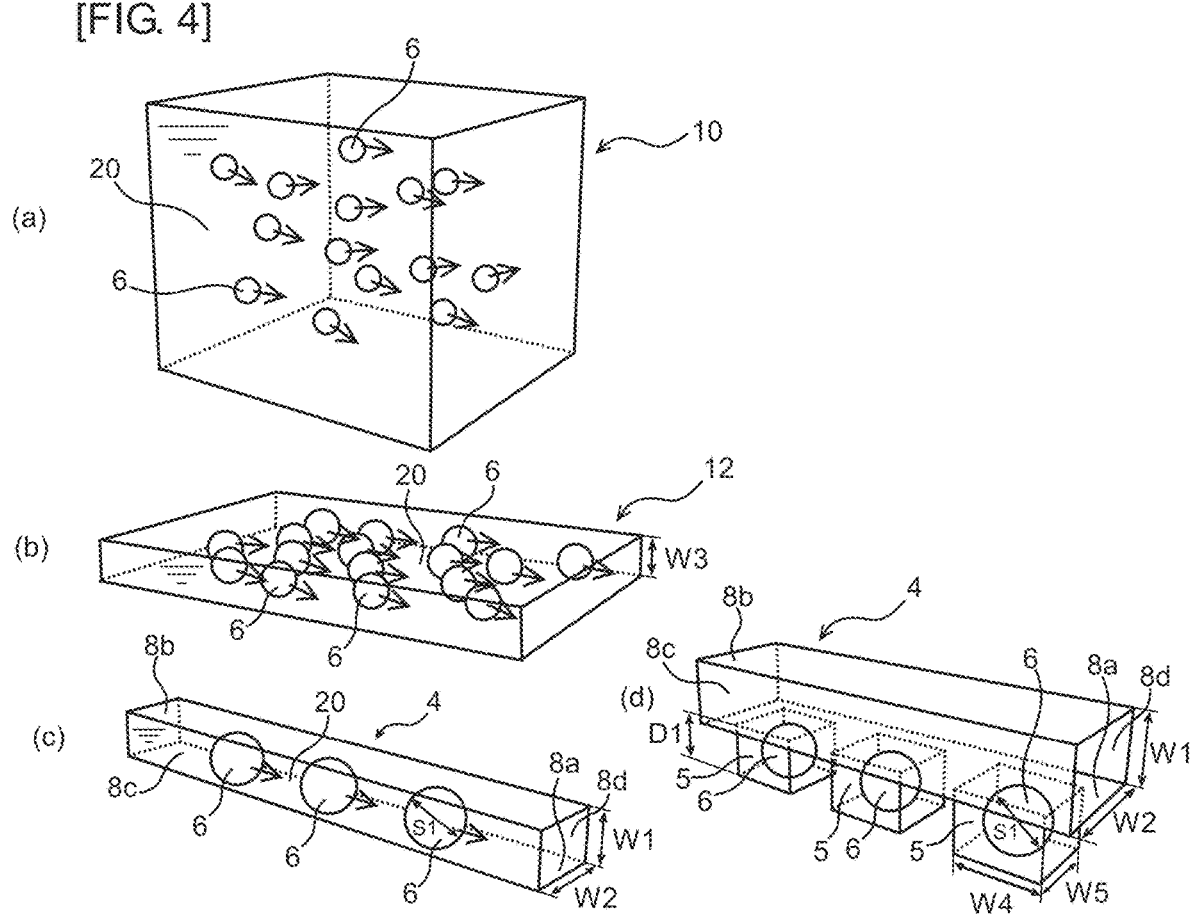
[FIG. 5]
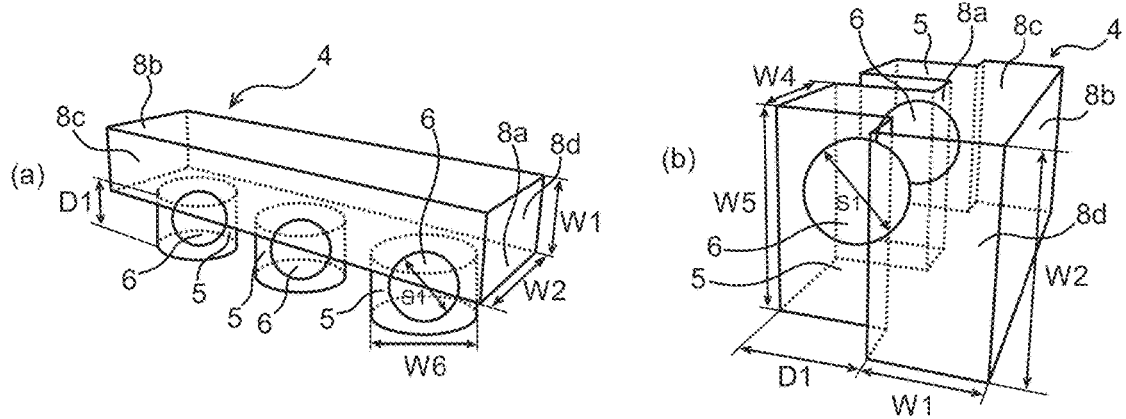

[FIG. 6]
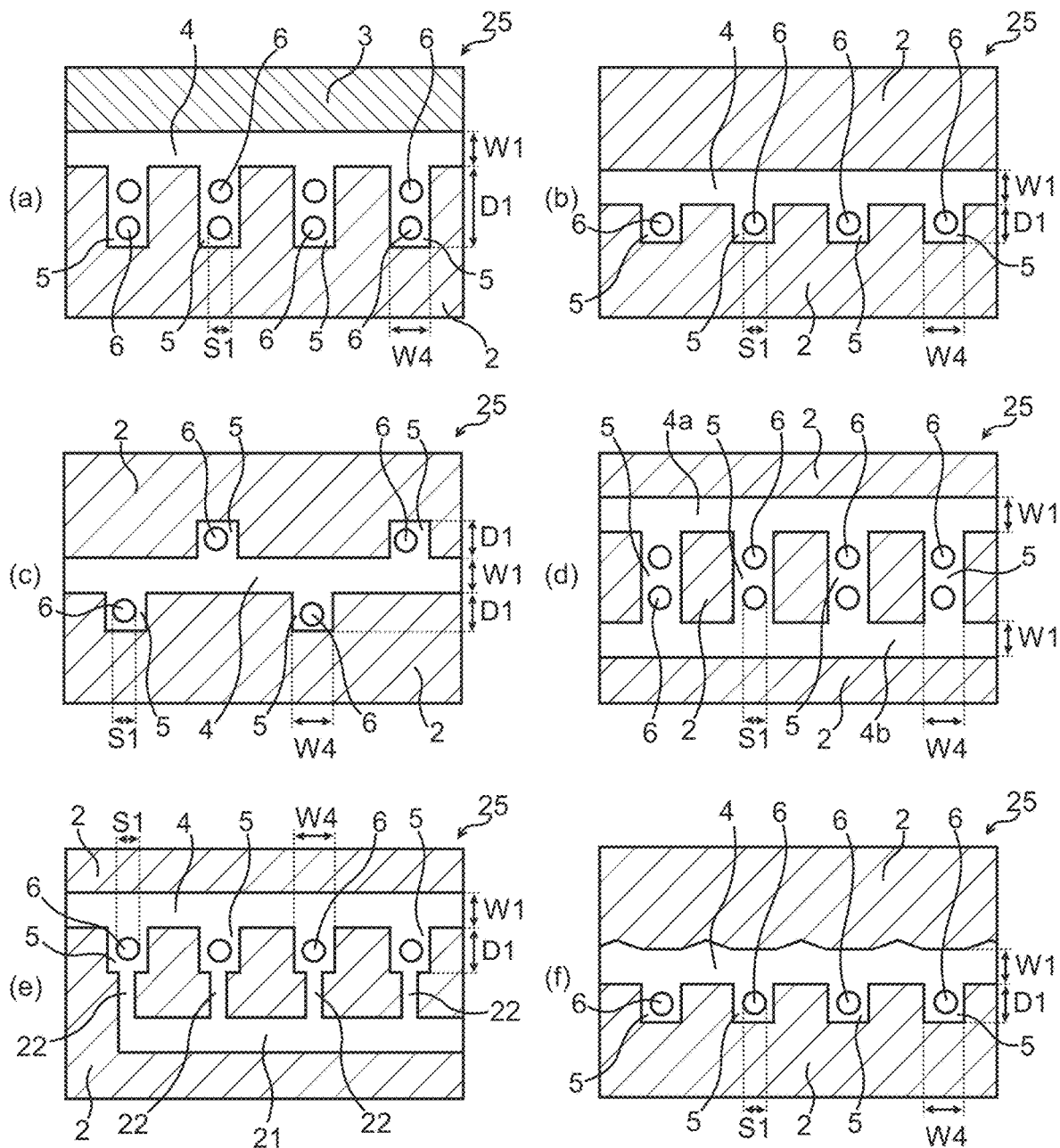

[FIG. 7]
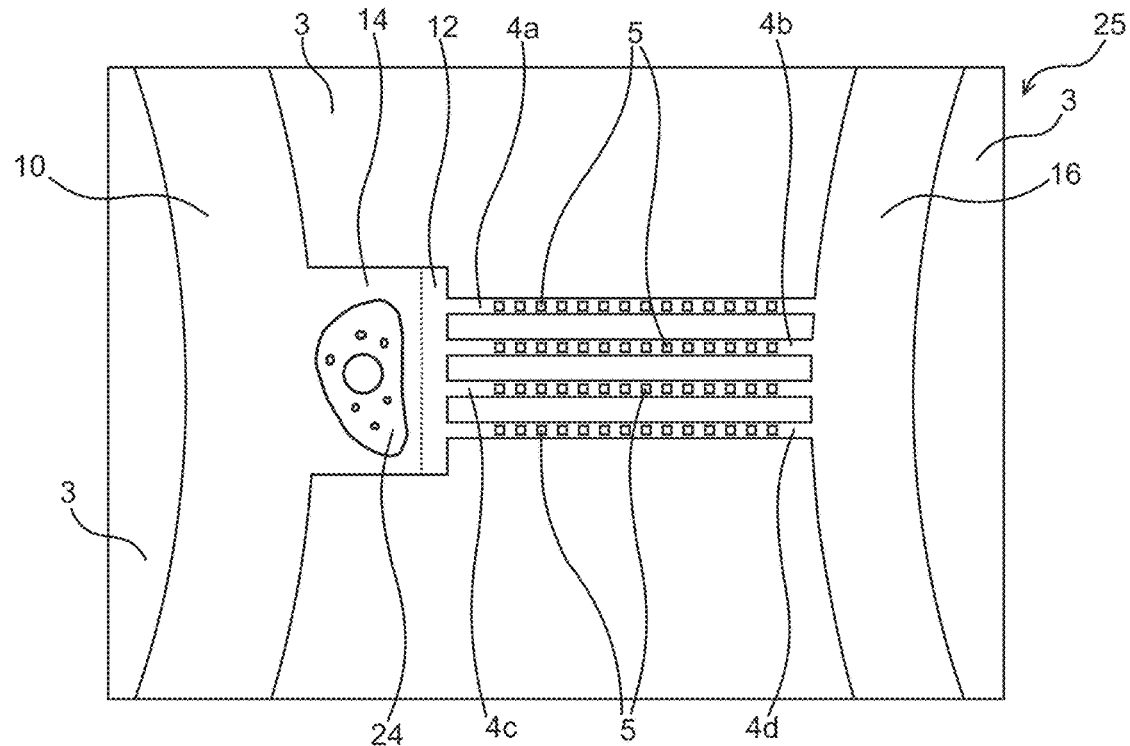
[FIG. 8]
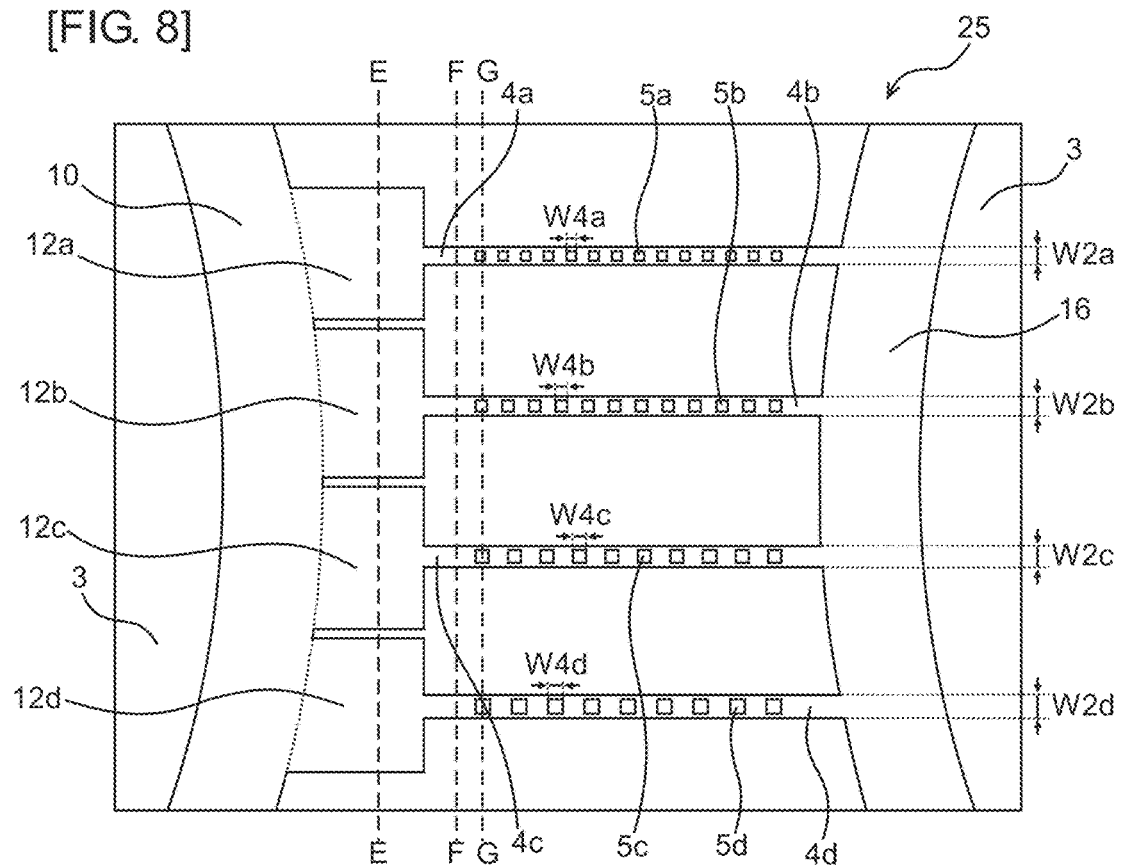

[FIG. 9]
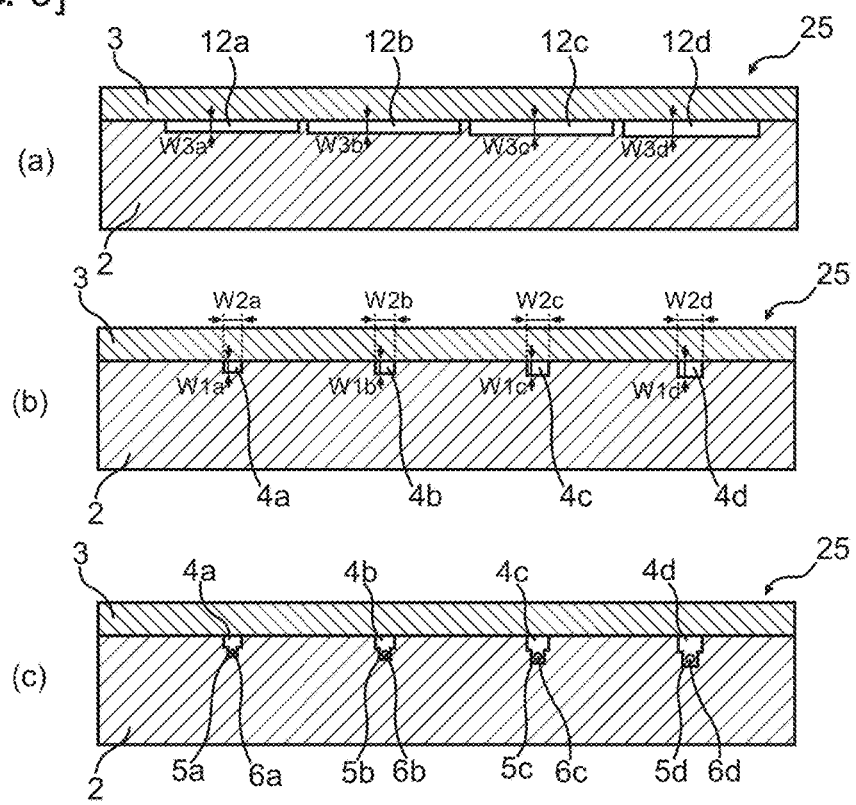
[FIG. 10]
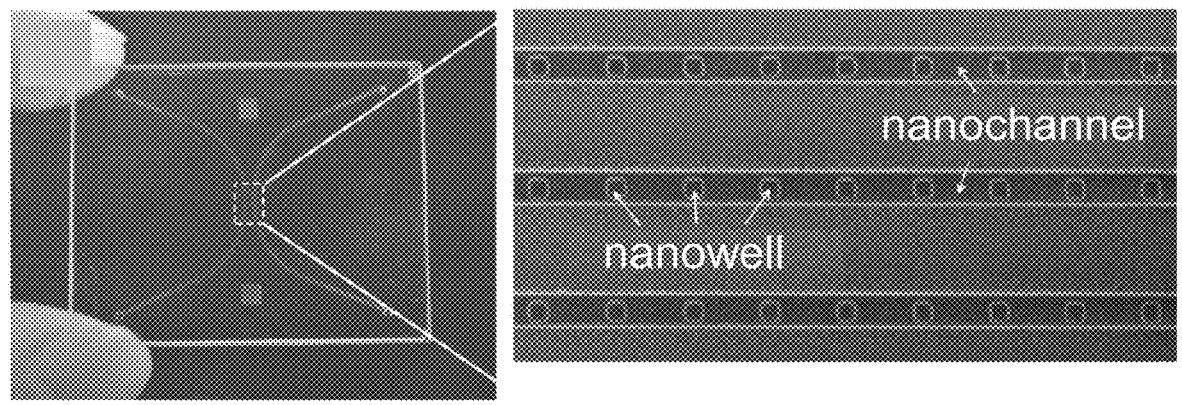

[FIG. 11]
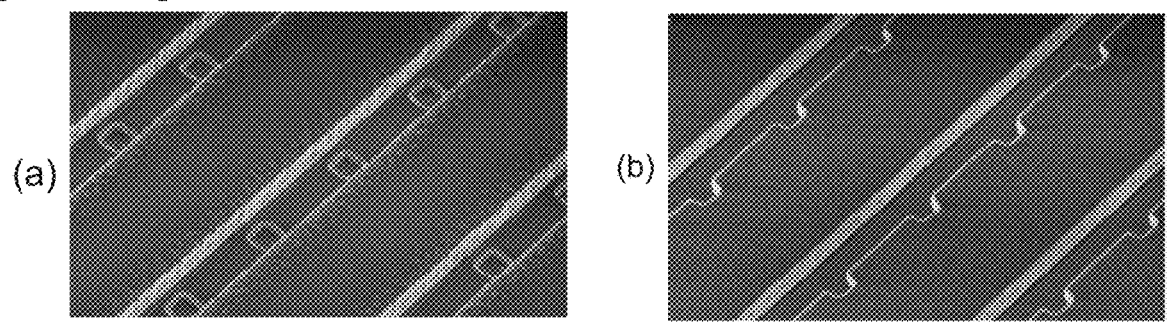
[FIG. 12]
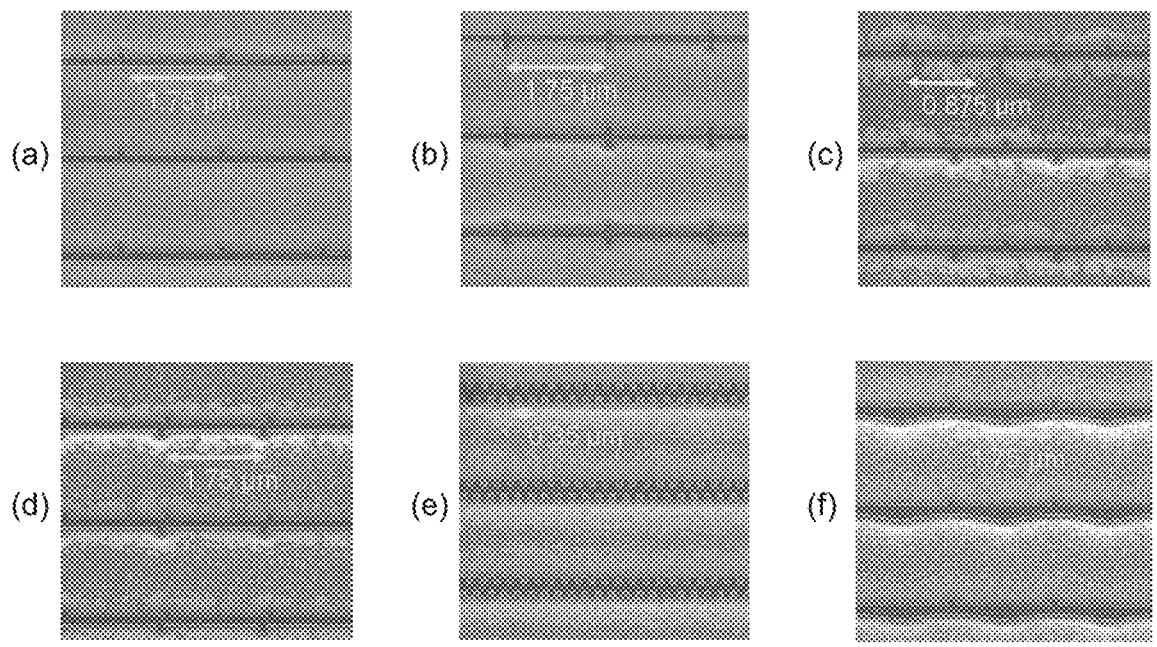

[FIG. 13]
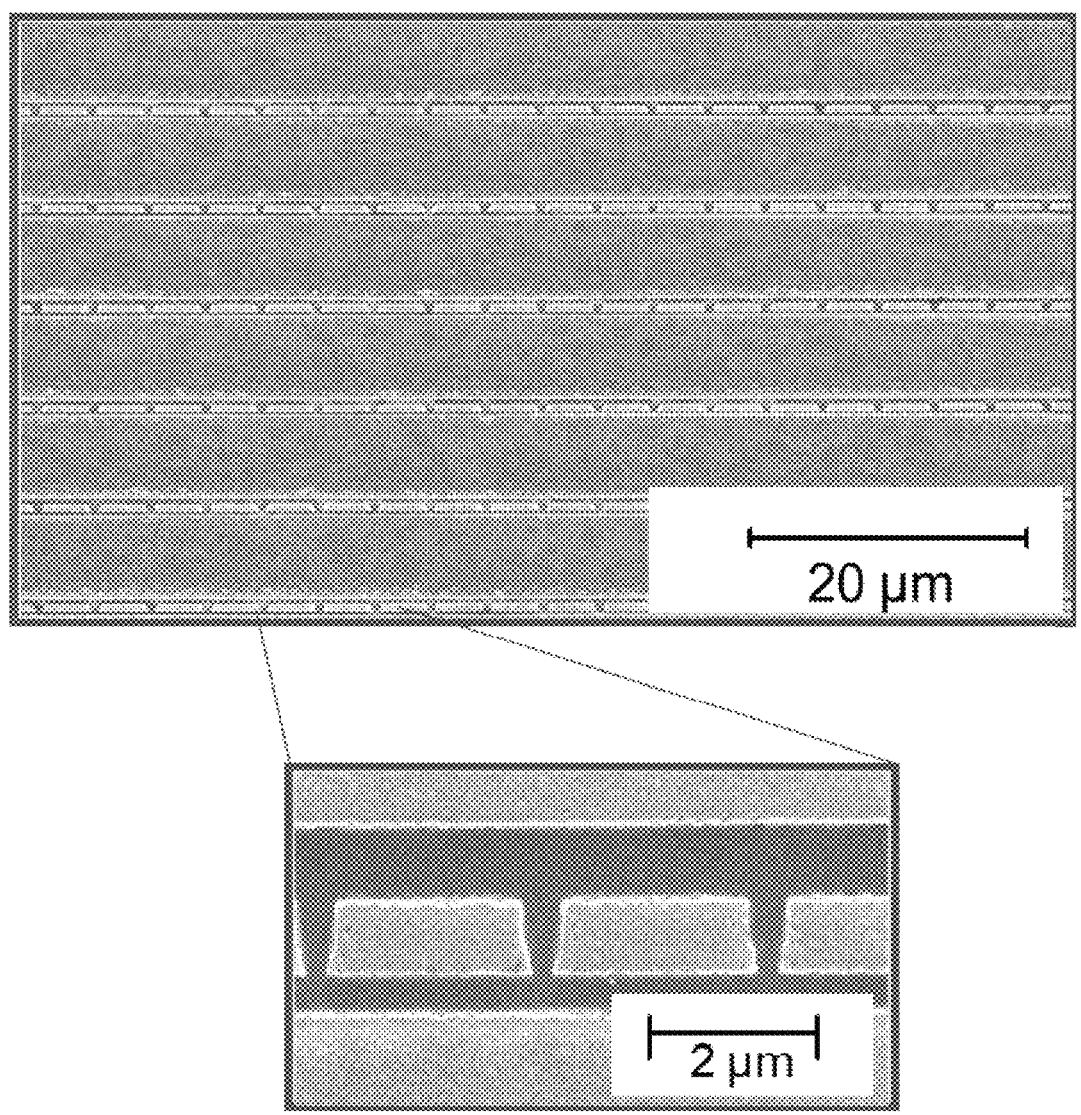

[FIG. 14]
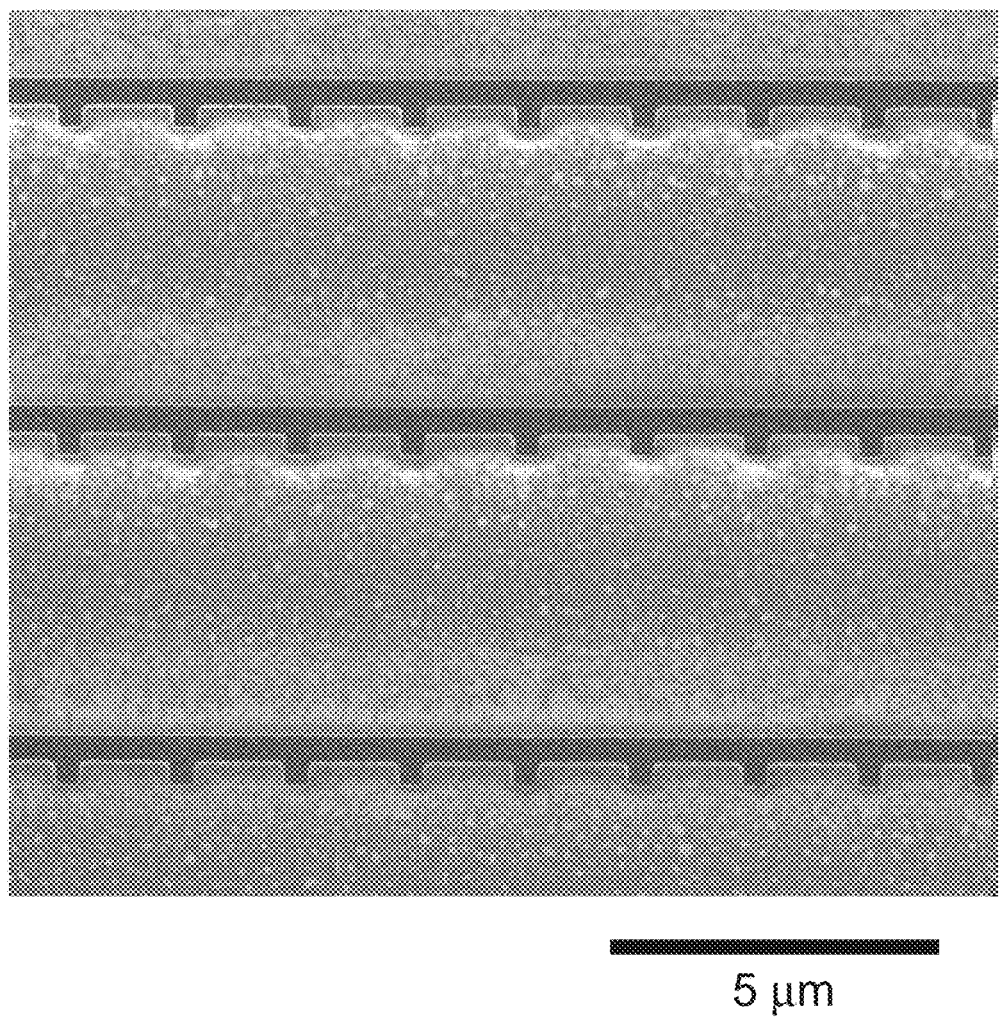
[FIG. 15]
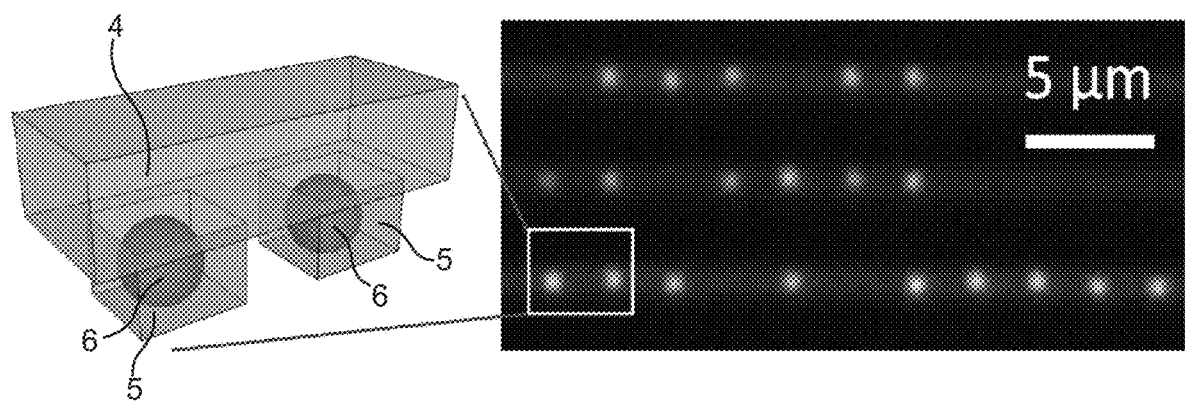

[FIG. 16]
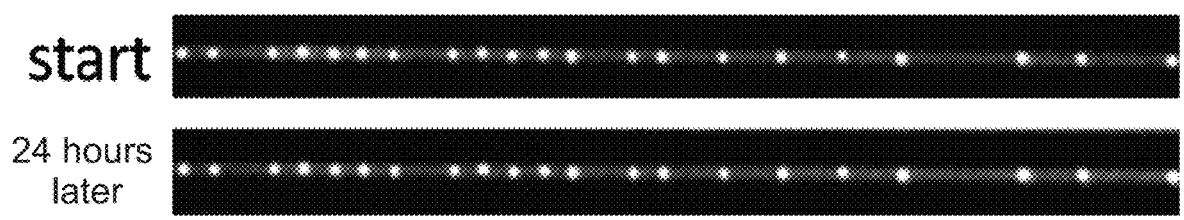
[FIG. 17]
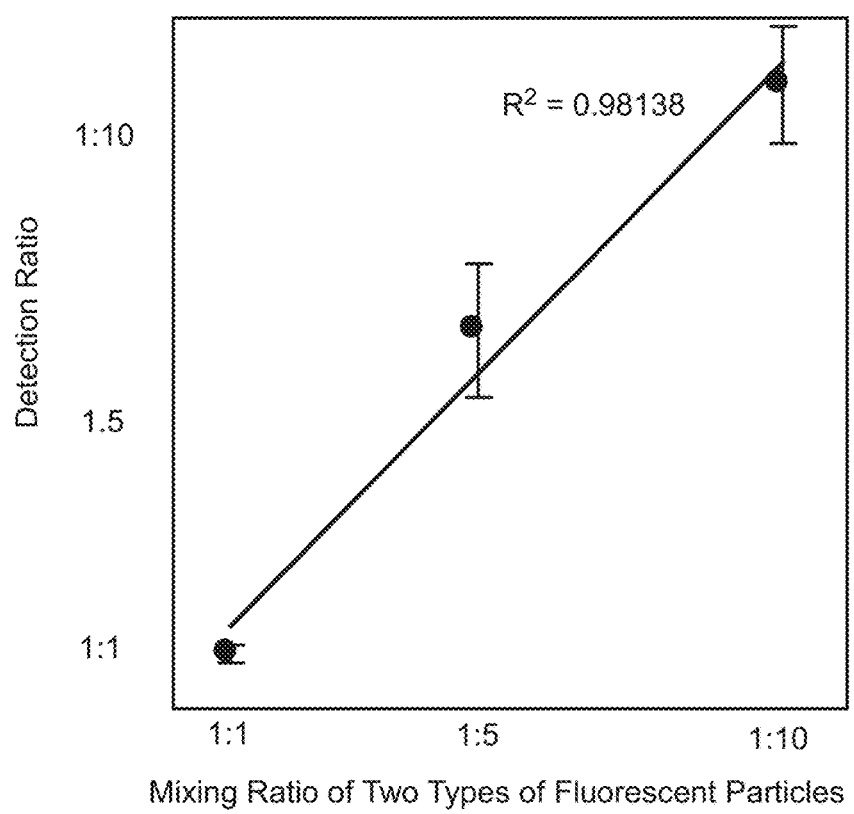

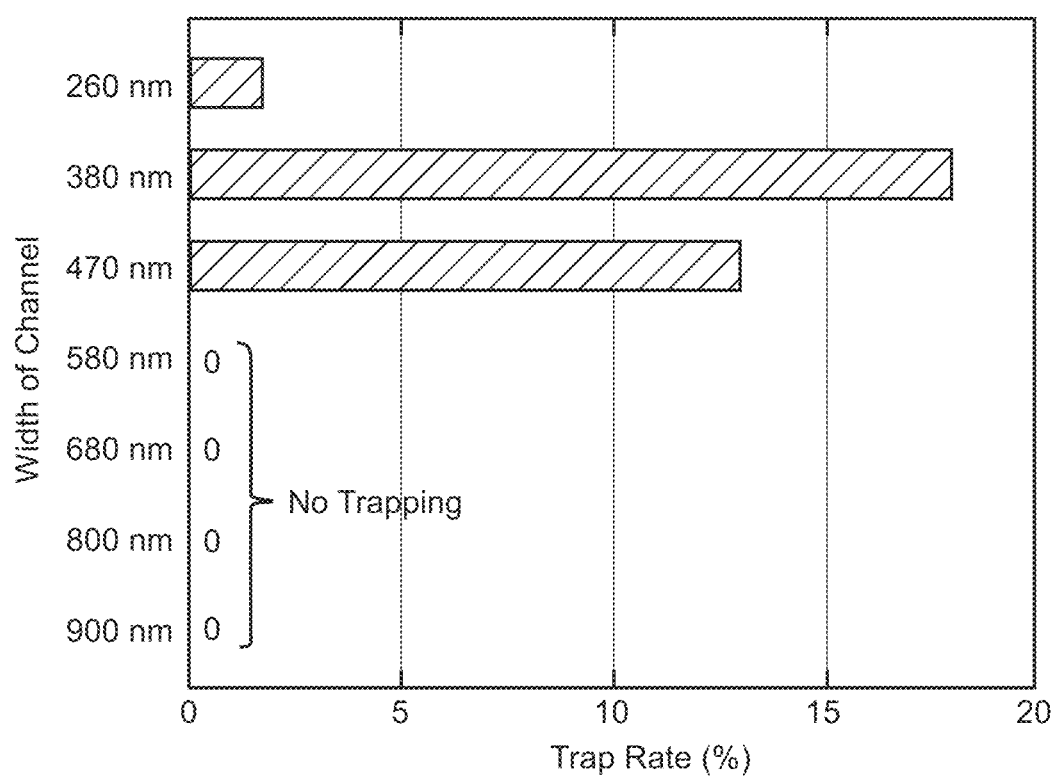
[FIG. 18]

[FIG. 19]
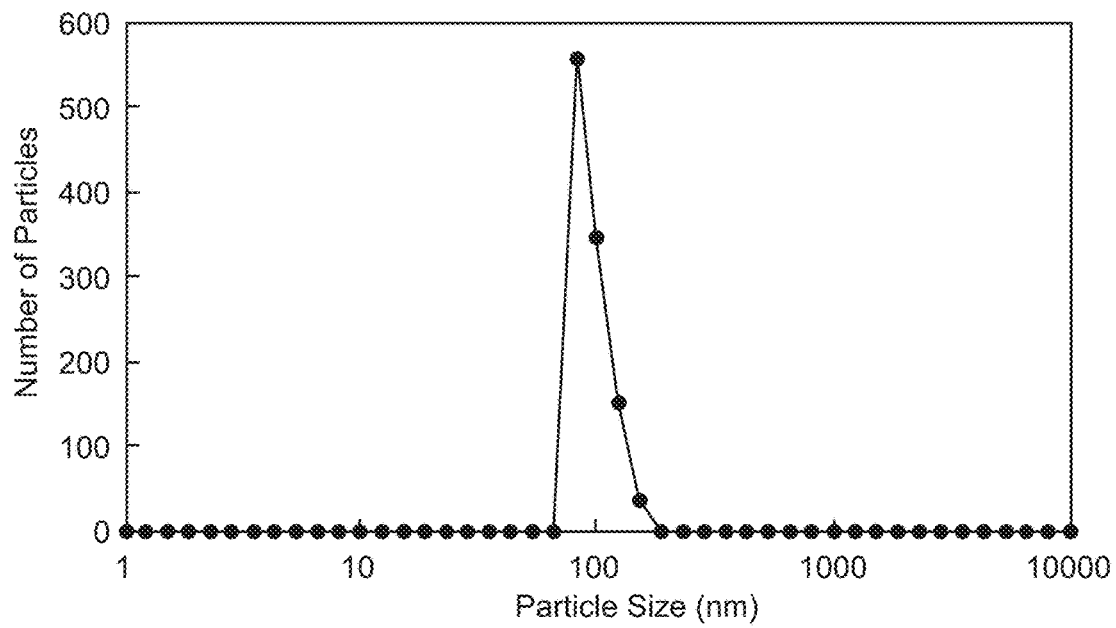
[FIG. 20]
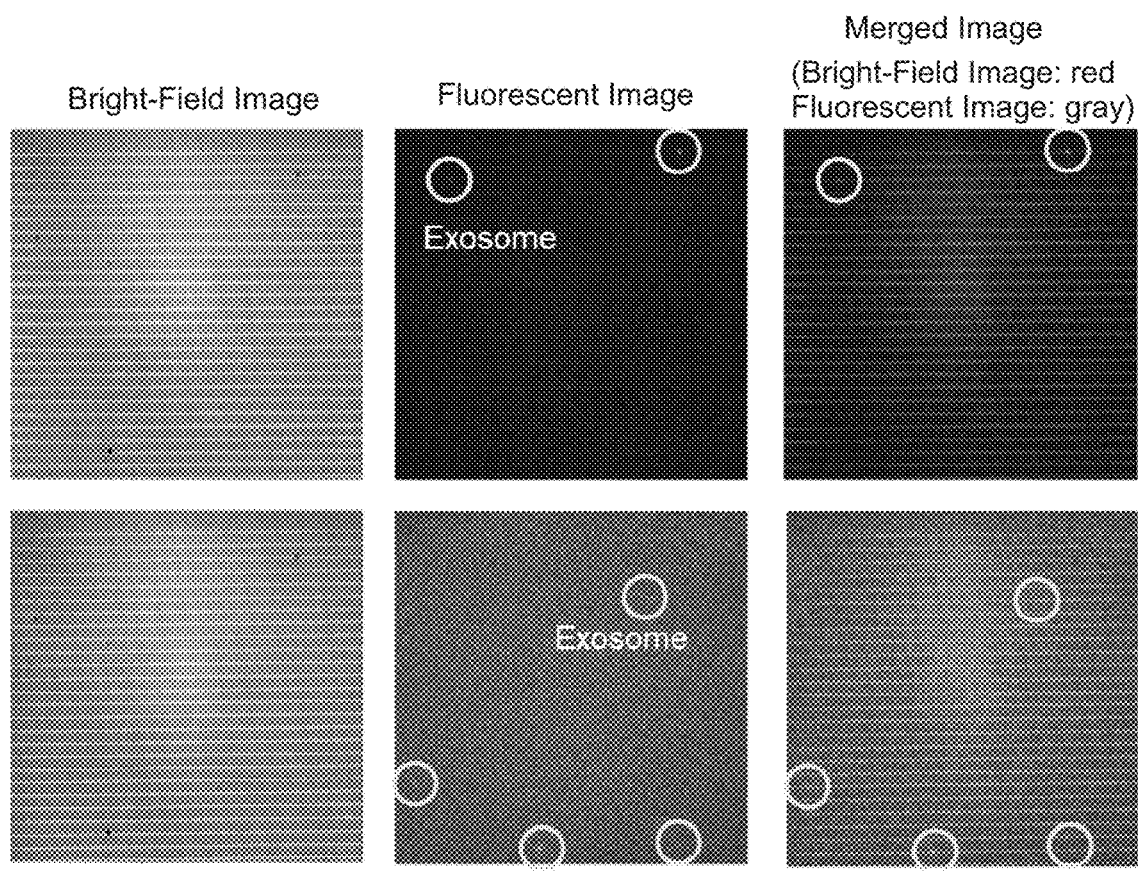

PARTICLE TRAPPING DEVICE AND PARTICLE TRAPPING METHOD

TECHNICAL FIELD

The present invention relates to a particle trapping device and a particle trapping method.

BACKGROUND ART

In fields of analytical chemistry, catalytic chemistry, biochemistry, optical devices, energy and biotechnology, medical field, etc., nanoparticles are often used in a liquid phase.

For example, cells secrete extracellular vesicles covered with a lipid bilayer membrane having various sizes. The extracellular vesicles are sorted according to their sizes and include exosomes (size: 50 to 200 nm), microvesicles (size: 200 to 1,000 nm), and so forth. Among them, the exosomes include various proteins, mRNA, microRNA, and the like; and it has been found during recent years that the exosomes have a key role in metastasis of cancer. Therefore, the exosomes are expected to be non-invasive biomarkers/therapeutic tools used for various diseases (see, for example, PTL 1).

In the meanwhile, viral infectious diseases lead to immense ill health of human beings and animals. It is necessary to identify infecting viruses in order to carry out early diagnosis of infectious diseases and to determine therapeutic strategies for dealing with the infectious diseases. The viruses are about 20 nm to 300 nm in size, and generally are collected and concentrated with use of a centrifugal separation method (see, for example, PTL 2).

Microchips are known to trap particles in a solution with use of projections disposed in a channel (see, for example, PTL 3).

CITATION LIST

Patent Literatures

[PTL 1] Japanese Unexamined Patent Application Publication No. 2017-40595
[PTL 2] Japanese Unexamined Patent Application Publication No. 2011-45358
[PTL 3] Japanese Unexamined Patent Application Publication No. 2002-233792

SUMMARY OF INVENTION

Technical Problems

To accurately control the nanoparticles spatiotemporally is an important subject and has a decisive influence on maximum exertion of characteristics of the nanoparticles and on discovery of new functions the nanoparticles. The nanoparticles exhibit active Brownian movement in the liquid phase; therefore, it is greatly difficult to control the nanoparticles in the liquid phase spatiotemporally. Moreover, to quantitatively analyze the nanoparticles such as the extracellular vesicles and the viruses has a number of challenges such as requiring troublesome isolated handling, low detection rates, expensive equipment for experiment, etc.

The present invention is developed in view of such circumstances, and provides a particle trapping device capable of confining target particle inside particle pit trap and of observing and analyzing the trapped target particle individually.

Solutions to Problems

The present invention provides a particle trapping device comprising: a lead-in channel; a flattened channel disposed on the downstream side of the lead-in channel; a rectangular channel disposed on the downstream side of the flattened channel; and a particle pit trap disposed at least on a first inner wall face of the rectangular channel, wherein the lead-in channel has a channel cross-section larger than a channel cross-section of the flattened channel; the flattened channel has a flat channel cross-section whose width is longer than its height; the rectangular channel has a rectangular channel cross-section, and is provided with the first inner wall face, a second inner wall face opposed to the first inner wall face, a third inner wall face, and a fourth inner wall face opposed to the third inner wall face; and wherein the lead-in channel, the flattened channel, the rectangular channel, and the particle pit trap are characterized by being configured in such a way that a portion of liquid containing target particles and flowing through the lead-in channel flows into the flattened channel; the target particles contained in the liquid that had flowed through the flattened channel flow into the rectangular channel; and the target particle that had flowed through the rectangular channel enter into the particle pit trap and is trapped therein.

Advantageous Effects of Invention

Since the particle trapping device according to the present invention comprises the lead-in channel, the flattened channel disposed on the downstream side of the lead-in channel, the rectangular channel disposed on the downstream side of the flattened channel, and the particle pit trap disposed at least on the first inner wall face of the rectangular channel, the device is capable of allowing the target particles-containing liquid to flow into the lead-in channel, the flattened channel, and the rectangular channel, and is also capable of allowing the target particle flowing through the rectangular channel to enter into the particle pit trap and to be trapped therein. This makes it possible to trap the target particle only by allowing a minute amount of the target particles-containing liquid to flow into the lead-in channel, the flattened channel, and the rectangular channel; and this also make it possible to easily separate and trap the target particle (only by using one chip) at low cost.

The flattened channel is disposed between the lead-in channel and the rectangular channel. The target particles can flow from the lead-in channel to the flattened channel; however, depending on a thickness of the flattened channel, the particles having a large size cannot flow from the lead-in channel to the flattened channel. Therefore, the particles in the liquid can be subjected to a filtering process with use of the flattened channel. Also, since the flattened channel has the flat channel cross-section, even if one of the particles that had flowed through the lead-in channel gets stuck in the flattened channel, the flattened channel would not be plugged. Therefore, owing to the flattened channel provided in the device, the flow of the liquid from the lead-in channel to the rectangular channel can be inhibited from being blocked.

The particle trapping device according to the present invention is capable of subjecting the target particle confined in the particle pit trap to the individual observation, analysis, and so forth. Moreover, since it is unnecessary to carry out ultracentrifugal separation, precipitating reagent treatment, etc., it is possible to observe, analyze, and so forth intact (or non-damaged) target particle at low cost. It is also possible to stably array the plurality of target particles for a prolonged time. Furthermore, it is possible to trap the target particle contained in a tiny amount of the liquid (for example, several pL of the liquid) in the particle pit trap and to observe and analyze the trapped target particle.

BRIEF DESCRIPTION OF DRAWINGS

FIG. 1 illustrates a diagrammatic top view of a particle trapping device in accordance with one embodiment of the present invention.

FIG. 2 illustrates a diagrammatic enlarged view of a portion surrounded by the dashed line A in the particle trapping device of FIG. 1.

FIG. 3(a) illustrates a diagrammatic cross-section view of the particle trapping device taken along the dashed line B-B of FIG. 2; FIG. 3(b) illustrates a diagrammatic cross-section view of the particle trapping device taken along the dashed-dotted line C-C of FIG. 2; and FIG. 3(c) illustrates a diagrammatic cross-section view of the particle trapping device taken along the dashed-dotted line D-D of FIG. 2.

FIG. 4(a) illustrates a diagrammatic view of a lead-in channel; FIG. 4(b) illustrates a diagrammatic view of a flattened channel; FIG. 4(c) illustrates a diagrammatic view of a rectangular channel; and FIG. 4(d) illustrates a diagrammatic view of a rectangular channel and particle pit traps.

FIG. 5(a) illustrates a diagrammatic view of a rectangular channel and particle pit traps provided in a particle trapping device in accordance with one embodiment of the present invention; and FIG. 5(b) illustrates a diagrammatic view of a rectangular channel and particle pit traps provided in a particle trapping device in accordance with one embodiment of the present invention.

FIGS. 6(a) to 6(f) each illustrate a diagrammatic cross-section view of a particle trapping device in accordance with one embodiment of the present invention.

FIG. 7 illustrates a diagrammatic top view of a particle trapping device in accordance with one embodiment of the present invention.

FIG. 8 illustrates a diagrammatic top view of a particle trapping device in accordance with one embodiment of the present invention.

FIG. 9(a) illustrates a diagrammatic cross-section view of the particle trapping device taken along the dashed line E-E of FIG. 8; FIG. 9(b) illustrates a diagrammatic cross-section view of the particle trapping device taken along the dashed line F-F of FIG. 8; and FIG. 9(c) illustrates a diagrammatic cross-section view of the particle trapping device taken along the dashed line G-G of FIG. 8.

FIG. 10 shows a photograph and an SEM image of a particle trapping device prepared in an experiment.

FIGS. 11(a) and 11(b) each show an SEM image of rectangular channels and particle pit traps formed on a first substrate.

FIGS. 12(a) to 12(f) each show an SEM image of rectangular channels and particle pit traps formed on a first substrate.

FIG. 13 shows an SEM image and its enlarged image of rectangular channels, particle pit traps, auxiliary channels, and connecting channels formed on a first substrate.

FIG. 14 shows an SEM image of rectangular channels and particle pit traps formed on a first substrate.

FIG. 15 shows a fluorescence microscopic image of fluorescent PS particles trapped in particle pit traps.

FIG. 16 shows fluorescence microscopic images exhibiting results of evaluation experiments in time stability.

FIG. 17 is a graph showing results of experiments on trapped mixed particles.

FIG. 18 is a graph showing results of measurement experiments in particle trap rates.

FIG. 19 shows particle size distribution of exosomes contained in a culture supernatant used for an experiment on trapped exosomes FIG. 20 shows bright field images, fluorescent images, and merged images thereof of a particle trapping device in which exosomes are trapped in particle pit traps.

DESCRIPTION OF EMBODIMENTS

The particle trapping device according to the present invention comprises: the lead-in channel; the flattened channel disposed on the downstream side of the lead-in channel; the rectangular channel disposed on the downstream side of the flattened channel; and the particle pit trap disposed at least on the first inner wall face of the rectangular channel, wherein the lead-in channel has the channel cross-section larger than the channel cross-section of the flattened channel; the flattened channel has a flat channel cross-section whose width is longer than its height; the rectangular channel has a rectangular channel cross-section, and is provided with the first inner wall face, a second inner wall face opposed to the first inner wall face, a third inner wall face, and a fourth inner wall face opposed to the third inner wall face; and wherein the lead-in channel, the flattened channel, the rectangular channel, and the particle pit trap are characterized by being configured in such a way that a portion of the liquid containing the target particles and flowing through the lead-in channel flows into the flattened channel; the target particles contained in the liquid that had flowed through the flattened channel flow into the rectangular channel; and the target particle that had flowed through the rectangular channel enter into the particle pit trap and is trapped therein.

It is desirable that a width between the first inner wall face and the second inner wall face of the rectangular channel is 1.04 times or more to 2.3 times or less an average particle diameter of the target particles. This enables the target particle flowing through the rectangular channel to efficiently enter into the particle pit trap and to be trapped therein. This was verified by experiments carried out by the inventors of the present invention.

It is desirable that a width between the third inner wall face and the fourth inner wall face of the rectangular channel provided in the particle trapping device according to the present invention is 1.04 times or more to 5 times or less the average particle diameter of the target particles. This enables the target particles to flow in a row through the rectangular channel, and makes it possible to increase probability of the target particles entering into the particle pit traps.

It is desirable that the particle pit trap provided in the particle trapping device according to the present invention has a size that is 1.04 times or more to 3 times or less the average particle diameter of the target particles. This enables the target particle flowing through the rectangular channel to enter into the particle pit trap, and makes it possible to inhibit the target particle that had entered into the particle pit trap from leaving the particle pit trap.

It is desirable that the particle trapping device according to the present invention comprises an auxiliary channel and a connecting channel. The auxiliary channel is configured to extend substantially parallel to the rectangular channel; and the connecting channel is configured to connect the particle pit trap to the auxiliary channel. This enables the liquid flowing through the rectangular channel to enter into the particle pit trap, then to flow through the connecting channel and the auxiliary channel; therefore, it makes it easy for the target particle to enter into the particle pit trap. The connecting channel is configured to have a channel cross-section that does not allow the target particle to pass through the connecting channel. For example, the connecting channel may be configured to have a width smaller than the average particle diameter of the target particles. This makes it possible to prevent the particle that had entered from the rectangular channel to the particle pit trap from flowing to the auxiliary channel, with the result that the particle can be trapped in the particle pit trap.

Moreover, letting the liquid flow from the auxiliary channel toward the particle pit trap makes it possible to collect the target particle trapped in the particle pit trap.

It is desirable that the particle trapping device according to the present invention is provided with the lead-in channel disposed on the upstream side of the rectangular channel. This enables the target particles-containing liquid to be supplied to the rectangular channel through the lead-in channel.

It is desirable that the flattened channel has a thickness (height) that is 1.04 times or more to 2.3 times or less the average particle diameter of the target particles. A structure like this allows the target particles to flow from the lead-in channel to the flattened channel, but does not allow the particles larger than the thickness of the flattened channel to flow from the lead-in channel to the flattened channel. Therefore, the particles in the liquid can be subjected to a filtering process with use of the flattened channel. Owing to the flat channel cross-section of the flattened channel, even if one of the particles that had flowed through the lead-in channel gets stuck in the flattened channel, the flattened channel would not be blocked. Therefore, owing to the flattened channel, it is inhibited that the flow of the liquid from the lead-in channel to the rectangular channel is interrupted.

It is desirable that the thickness (height) of the flattened channel is configured to be substantially the same as a width between the first inner wall face and the second inner wall face or a width between the third inner wall face and the fourth inner wall face; and it is desirable that one of an upper plane and a lower plane of the flattened channel is configured to substantially match up with the first inner wall face or the third inner wall face and that the other one of the upper plane and the lower plane is configured to substantially match up with the second inner wall face or the fourth inner wall face. This enables the target particles flowing with the liquid through the flattened channel to flow easily into the rectangular channel.

It is desirable that the particle trapping device according to the present invention also have a cell trapping chamber disposed between the rectangular channel and the lead-in channel. This cell trapping chamber is to trap cells and may allow the trapped cells to secrete extracellular vesicles. The cell trapping chamber allows the extracellular vesicles to flow into the flattened channel and the rectangular channel; and the particle pit trap can trap the extracellular vesicles therein.

It is desirable that the particle trapping device according to the present invention comprises a first substrate and a second substrate; and it is desirable that the rectangular channel has a structure in such a way that grooves formed on the first substrate are covered with the second substrate. This enables the particle pit trap, the rectangular channel, the flattened channel, the lead-in channel, etc. to be formed between the first substrate and the second substrate.

It is desirable that the particle trapping device according to the present invention is configured in such a way that the particle pit trap traps the target particle therein.

It is desirable that the target particles are follicles, organelles, extracellular vesicles, viruses, liposomes, metallic particles, organic particles, inorganic particles, air pollution particulates, or pollens.

The present invention also provides the particle trapping device comprising: the lead-in channel; the flattened channel; the rectangular channel having the rectangular cross-section; and the particle pit trap disposed on the first inner wall face of the rectangular channel, wherein the lead-in channel and the flattened channel are characterized by being configured in such a way that a portion of the liquid containing the target particles and flowing through the lead-in channel flows into the flattened channel; the rectangular channel is characterized by being configured in such a way that a portion of the liquid containing the target particles and flowing through the flattened channel flows into the rectangular channel; and the particle pit trap is characterized by being configured in such a way that the target particle flowing through the rectangular channel enter into the particle pit trap and is trapped therein.

The present invention also provides a particle trapping method characterized by comprising the steps of: allowing liquid containing target particles to flow into a lead-in channel; allowing the target particles-containing liquid to flow from the lead-in channel to a flattened channel; allowing the target particles-containing liquid to flow from the flattened channel to a rectangular channel; and allowing the target particle to enter into a particle pit trap formed on a first inner wall face of the rectangular channel and to be trapped in the pit trap. The particle trapping method according to the present invention make it possible to inhibit the channels from being blocked and to easily separate and trap the target particles at low cost.

In the following, one embodiment of the present invention will be described through the use of drawings. Note that compositions indicated in the drawings and the following descriptions are exemplifications and are not to limit the present invention only to the drawings and the following descriptions.

FIGS. 1 to 9 illustrate particle trapping devices in accordance with the present embodiment. The descriptions of the drawings are as described above.

A particle trapping device 25 of the present embodiment comprises: a lead-in channel 10; a flattened channel 12 disposed on the downstream side of the lead-in channel 10; a rectangular channel 4 disposed on the downstream side of the flattened channel 12; and a particle pit trap 5 disposed at least on an inner wall face 8a of the rectangular channel 4, wherein the lead-in channel 10 has a channel cross-section larger than a channel cross-section of the flattened channel 12; the flattened channel 12 has a flat channel cross-section whose width is longer than its height; the rectangular channel 4 has a rectangular channel cross-section, and is provided with the inner wall face 8a, a inner wall face 8b opposed to the inner wall face 8a, a inner wall face 8c, and a inner wall face 8d opposed to the inner wall face 8c; and wherein the lead-in channel 10, the flattened channel 12, the rectangular channel 4, and the particle pit trap 5 are characterized by being configured in such a way that a portion of liquid containing target particles 6 and flowing through the lead-in channel 10 flows into the flattened channel 12; the target particles 6 contained in the liquid that had flowed through the flattened channel 12 flow into the rectangular channel 4; and the target particle 6 that had flowed through the rectangular channel 4 enter into the particle pit trap 5 and is trapped therein.

A particle trapping method in accordance with the present embodiment is characterized by comprising the steps of: allowing liquid containing target particles 6 to flow into a lead-in channel 10; allowing the target particles 6-containing liquid to flow from the lead-in channel 10 to a flattened channel 12; allowing the target particles 6-containing liquid to flow from the flattened channel 12 to a rectangular channel 4; and allowing the target particle 6 to enter into a particle pit trap 5 formed on a first inner wall face 8a of the rectangular channel 4 and to be trapped in the pit trap.

In the following, the particle trapping device 25 and the particle trapping method in accordance with the present embodiment will be described.

The particle trapping device 25 is to trap the target particle 6 inside the particle pit trap 5. The particle trapping device 25 may be a particle separation device or may be a channel structure. Also, the particle trapping device 25 may function as an extracellular vesicle trapping device, a virus trapping device, or a pollen trapping device.

The target particles 6 are an object to be trapped by the particle trapping device 25 and have a certain range of a particle diameter. An average particle diameter of the target particles 6 is considered an average value of this diameter range. For example, in a case where the particles to be trapped have a diameter range from 90 nm or more to 110 nm or less, an average particle diameter of the target particles 6 is 100 nm. The particle trapping device 25 can trap the target particles 6 having different diameter ranges.

Examples of the target particles 6 include follicles, organelles, extracellular vesicles (exosomes, microvesicles, etc.), viruses, liposomes, metallic particles, organic particles, inorganic particles, air pollution particulates (suspended particulate matters, PM 2.5, etc.), and pollens.

Examples of a liquid 20 containing the extracellular vesicles (target particles 6) include blood serum, blood plasma, urine, culture supernatant, saliva, amniotic fluid, malignant ascites, cerebrospinal fluid (CSF), gastrointestinal fluid (GI), inflammatory fluid, lymph fluid, and alveolar lavage fluid.

An average particle diameter of the target particles 6 is, for example, from 5 nm or more to 100 μm or less; and preferably 50 nm or more to 2 μm or less, and more preferably 80 nm or more to 1 μm or less.

The particle trapping device 25 is not limited in its structure, as long as the device is configured to comprise the rectangular channel 4, the particle pit trap 5, and so forth; and the device may be configured to have, for example, a structure in which a first substrate 2 and a second substrate 3 are layered. In this case, the first substrate 2 may have grooves formed thereon that become the rectangular channel 4, the particle pit trap 5, etc.; and the second substrate 3 may adhere to a surface of the first substrate 2 where the grooves are formed. This enables the rectangular channel 4, the particle pit trap 5, etc. to be formed between the first substrate 2 and the second substrate 3.

The first substrate 2 and the second substrate 3 each may be made of an inorganic material or may be made of an organic material. It is preferable that the material of the first substrate 2 and of the second substrate 3 is transparent. This enables the particles trapped (or captured) by the particle trapping device 25 to be optically observed and analyzed.

Examples of the first substrate 2 or the second substrate 3 include a glass substrate (such as a quartz glass substrate), a semiconductor substrate (such as a silicon substrate), and a ceramic substrate. It is particularly preferable that the first substrate 2 and the second substrate 3 are made of the glass substrate. Since glass usually has a hydroxyl group (—OH) on its surface, the glass allows an inner face of the rectangular channel 4, etc. to become hydrophilic. This enables water, a buffer solution, or an aqueous solution (liquid 20) to flow into the rectangular channel 4, etc. by capillary action. Since the glass substrate is transparent, the target particle 6 confined (or trapped) inside the particle pit trap 5 can be optically observed. The glass substrate is also capable of subjecting the target particles 6 to optical processing.

The grooves to become the rectangular channel 4, the particle pit trap 5, etc. can be formed by etching the first substrate 2. For example, the first substrate 2 is covered with a resist material; and then parts of the resist film are removed (or eliminated) by an electron beam, forming a resist pattern on the resist film. Then the resist film, as an etching mask, is subjected to etching; and parts of the first substrate 2 are removed (or eliminated), forming grooves. By repeating such an etching process several times, grooves to become desired channels or pit traps can be formed on the first substrate 2. Also a groove to become the lead-in channel 10 or an exit-side channel 16 can be formed on the first substrate 2 or the second substrate 3 by photolithography and an etching technique. After this process, the first substrate 2 and the second substrate 3 are bonded; and the particle trapping device 25 is prepared in which the desired channels are formed.

The first substrate 2 and the second substrate 3 may adhere to each other by thermal bonding or by fusion bonding. Or the first substrate 2 and the second substrate 3 may be subjected to a plasma treatment; and a plasma-treated surface of the first substrate 2 may be brought into contact with a plasma-treated surface of the second substrate 3, making the first substrate 2 and the second substrate 3 adhere to each other.

Moreover, the first substrate 2 and the second substrate 3 may have channels and pit traps formed therebetween by forming grooves on both the first substrate 2 and the second substrate 3.

The particle trapping device 25 may be configured to have the lead-in channel 10. The lead-in channel 10 is to supply the target particles 6-containing liquid 20 to the rectangular channel 4. The lead-in channel 10 is configured to have a channel cross-section larger than a channel cross-section of the rectangular channel 4 or a channel cross-section of the flattened channel 12. The liquid 20 flowing through the lead-in channel 10 may contain particles having various particle diameters in addition to the target particles 6. The liquid 20 may also contain electrolytes such as KCl.

The lead-in channel 10 may be configured in such a way that the liquid 20 enters into an inlet port 18a, flows through the lead-in channel 10, and is discharged from an outlet port 19a. The lead-in channel 10 may also be configured in such a way that a portion of the liquid 20 flowing through the lead-in channel 10 flows into the flattened channel 12. By configuring the lead-in channel 10 in this way, the particles whose diameter is larger than a thickness (height) of the flattened channel 12 out of the particles in the liquid 20 do not enter into the flattened channel 12 but flow toward the outlet port 19a, while the particles whose diameter is smaller than the thickness of the flattened channel 12 enter into the flattened channel 12. This makes it possible to filter the particles, which flow with the liquid 20 to the flattened channel 12, at an inflow port of the flattened channel 12.

The lead-in channel 10 may be disposed on the first substrate 2 or on the second substrate 3; however, it is preferable that the lead-in channel is disposed on the second substrate 3. For example, the lead-in channel 10 may be configured to be provided in the particle trapping device 25 as illustrated in FIG. 1, FIG. 2, and FIG. 3(a).

The channel cross-section of the lead-in channel 10 may be shaped like a rectangle or may be shaped like a circle.

The lead-in channel 10 may be configured to have the channel cross-section whose size is 10 times or more a largest diameter of the particles out of the particles in the liquid 20 entering through the inlet port 18a. This makes it possible to inhibit the particles from plugging up the lead-in channel 10 and to inhibit the flow of the particles from being blocked in the lead-in channel 10. For example, in a case where the liquid 20 contains various particles having a diameter of 1,000 nm or less, the lead-in channel 10 may be configured to have a size of 10 μm or more.

In the case where the channel cross-section of the lead-in channel 10 is shaped like the rectangle, a size of the lead-in channel 10 is considered lengths of sides of the channel cross-section; and in the case where the channel cross-section of the lead-in channel 10 is shaped like the circle, a size of the lead-in channel is considered a diameter of the channel cross-section.

A largest particle diameter of the particles out of the particles in the liquid 20 may be designed as a particle diameter for filtration accuracy of a filter to be used for a filtering process that is carried out before the liquid 20 is injected into the inlet port 18a. For example, in a case where the liquid 20 is subjected to a filtering process with use of a 0.45-μm filter, a largest particle diameter of the particles out of the particles in the liquid 20 may be configured to be 450 nm.

The liquid 20 and the particles contained in the liquid 20 flow all together through the lead-in channel 10 in a flow direction of the liquid 20; however, the particles move around three-dimensionally. For example, the particles may flow through the lead-in channel 10 in a vertical direction, a horizontal direction, and a front-back direction, as illustrated in FIG. 4(a).

The lead-in channel 10 may be configured in such a way that the liquid 20 entering through the inlet port 18a flows through the lead-in channel 10 by capillary action. This makes a pump or the like unnecessary and enables the device to be simplified. For example, by dripping the target particles 6-containing liquid 20 into the inlet port 18a, the liquid 20 may flow to the lead-in channel 10.

The lead-in channel 10 may be configured in such a way that the target particles 6-containing liquid 20 flows through the lead-in channel 10 with use of the pump. This allows for the stable flow of the liquid 20 into the lead-in channel 10, and enables the liquid 20 to be stably supplied to the rectangular channel 4. Also, the pump may allow a cleaning liquid to flow through the lead-in channel 10. To remove the liquid from the lead-in channel 10, the rectangular channel 4, and so forth, gas such as air may flow through the lead-in channel 10.

Before being injected into the inlet port 18a, the liquid 20 may be subjected to the filtering process. This enables the large particles that could possibly clog the lead-in channel 10 to be removed from the liquid 20, and inhibits the lead-in channel 10 from being clogged with the large particles. For example, a filtrate, which is the liquid 20 having been filtered through a 0.22-μm filter, a 0.45-μm filter, or the like, may be injected through the inlet port 18a into the lead-in channel 10. A supernatant liquid, which is the liquid 20 having been subjected to centrifuge separation, may be injected through the inlet port 18a into the lead-in channel 10.

The lead-in channel 10 and the flattened channel 12 may be configured to have a cell trapping chamber 14 placed therebetween. This cell trapping chamber 14 traps cells (or a single cell) 24 and may allow the trapped cells (or a single cell) 24 to secrete extracellular vesicles. The cell trapping chamber allows the extracellular vesicles to flow into the flattened channel 12 and the rectangular channel 4; and the particle pit trap 5 traps the extracellular vesicles. Upon providing stimulation caused by a cytokine, a hormone, etc., mechanical stimulation, optical stimulation, chemical stimulation, radiation stimulation, etc. to the cells (or a single cell) trapped in the cell trapping chamber 14, the extracellular vesicles secreted from the cells (or a single cell) may be trapped in the particle pit trap 5, and may be observed and analyzed. In this case, the lead-in channel 10 has the channel cross-section larger than the cells 24 to be trapped in the cell trapping chamber 14. Even when the cells trapped in the cell trapping chamber 14 do not receive any stimulation, the extracellular vesicles that had been secreted from the cells may also be trapped in the particle pit trap 5, and may be observed and analyzed.

The cell trapping chamber 14 may be configured to be provided in the particle trapping device 25 as illustrated in FIG. 7 as an example.

The particle trapping device 25 may have the flattened channel 12 placed between the rectangular channel 4 and the lead-in channel 10. The flattened channel 12 may be configured in such a way that the liquid 20 that had flowed through the lead-in channel 10 flows to the flattened channel 12; and the liquid 20 that had flowed through the flattened channel 12 flows to the rectangular channel 4. The flattened channel 12 has the channel cross-section configured to be flat shape, that is, thin in thickness W3 and wide in breadth. The thickness W3 of the flattened channel 12 may change in a stepwise fashion.

The inflow port where the liquid 20 flows from the lead-in channel 10 to the flattened channel 12 may be configured to have the same shape as the channel cross-section of the flattened channel 12.

For example, the flattened channel 12 may be configured to be provided in the particle trapping device 25 as illustrated in FIG. 1, FIG. 2, and FIGS. 3(a) and 3(b).

The flattened channel 12 has the thickness W3 that is 1.04 times or more to 2.3 times or less an average particle diameter S1 of the target particles 6. This allows the target particles 6 to flow from the lead-in channel 10 to the flattened channel 12, but does not allow the particles larger than the thickness W3 of the flattened channel 12 to flow from the lead-in channel 10 to the flattened channel 12. Therefore, the particles in the liquid 20 can be subjected to a filtering process with use of the flattened channel 12. Owing to the flat channel cross-section of the flattened channel 12, even if one of the particles that had flowed through the lead-in channel 10 gets stuck in the flattened channel 12, the flattened channel 12 would not be blocked. Therefore, owing to the flattened channel 12, it is inhibited that the flow of the liquid 20 from the lead-in channel 10 to the rectangular channel 4 is interrupted.

In a case where particles ranging from 90 nm or more to 110 nm or less in diameter need to be trapped by the particle trapping device 25, target particles 6 may be configured to be 100 nm in average particle diameter. In such a case, the thickness W3 of the flattened channel 12 may be configured to be 110 nm or more to 220 nm or less. In a case where particles ranging from 950 nm or more to 1,050 nm or less in diameter need to be trapped by the particle trapping device 25, target particles 6 may be configured to be 1,000 nm in average particle diameter. In such a case, the thickness W3 of the flattened channel 12 may be configured to be 1,100 nm or more to 2,200 nm or less.

The thickness W3 of the flattened channel 12 may be configured to be the same as a width W1 or a width W2 of the rectangular channel 4, or may be configured to be thinner than the width W1 or W2. This makes it possible to prevent the particles having a diameter large enough to possibly clog the rectangular channel 4 from flowing into the rectangular channel 4, and makes it also possible to inhibit the rectangular channel 4 from being clogged with such particles. Furthermore, in a case where the thickness W3 of the flattened channel 12 changes in a stepwise fashion, and the flattened channel 12 connects with a plurality of rectangular channels 4, the thickness W3 of the flattened channel 12 may be configured to be the same as the width W1 or W2 of the rectangular channel 4 adjacent to the flattened channel, or may be configured to be thinner than the width W1 or W2.

As illustrated in FIGS. 1 to 3 and FIG. 6(a), in a case where the particle pit trap 5 is disposed on the inner wall face 8a on the first substrate 2 side of the rectangular channel 4 (i.e., a bottom of the groove disposed on the first substrate 2), a thickness of the flattened channel 12 may be configured to be substantially the same as a width between the inner wall face 8a on the first substrate 2 side of the rectangular channel 4 (i.e., the bottom of the groove disposed on the first substrate 2) and the inner wall face 8b on the second substrate 3 side of the rectangular channel 4. In such a case, an upper plane of the flattened channel 12 (i.e., a surface on the second substrate 3 side) may be configured to substantially match up with (or correspond to) the inner wall face 8b on the second substrate 3 side of the rectangular channel 4; and a lower plane of the flattened channel 12 (i.e., a surface on the first substrate 2 side) may be configured to substantially match up with (or correspond to) the inner wall face 8a on the first substrate 2 side (i.e., the bottom of the groove disposed on the first substrate 2) of the rectangular channel 4.

As illustrated in FIG. 5(b) and FIG. 6(b) to FIG. 6(f), in a case where the particle pit trap 5 is disposed on a side face of the rectangular channel 4 (i.e., the inner wall face 8a or a side face of the groove disposed on the first substrate 2), a thickness of the flattened channel 12 may be configured to be substantially the same as a width between the inner wall face 8d on the first substrate 2 side (i.e., the bottom of the groove disposed on the first substrate 2) of the rectangular channel 4 and the inner wall face 8c on the second substrate 3 side of the rectangular channel 4. In such a case, the upper plane of the flattened channel 12 (i.e., the surface on the second substrate 3 side) may be configured to substantially match up with (or correspond to) the inner wall face 8c on the second substrate 3 side of the rectangular channel 4; and the lower plane of the flattened channel 12 (i.e., the surface on the first substrate 2 side) may be configured to substantially match up with (or correspond to) the inner wall face 8d on the first substrate 2 side (i.e., the bottom of the groove disposed on the first substrate 2) of the rectangular channel 4.

The target particles 6 flowing through the flattened channel 12 are limited in their movement by an upside inner wall face (i.e., an upper plane) and a downside inner wall face (i.e., a lower plane) of the flattened channel 12; therefore, the target particles 6 flow two-dimensionally. For example, the target particles 6 flow through the flattened channel 12 as illustrated in FIG. 4(b).

The particle trapping device 25 may be configured to have a plurality of flattened channels 12 as illustrated in FIG. 8. In this case, the flattened channels 12 may be configured to connect with rectangular channels 4, respectively; and the thickness W3 of the flattened channels 12 may be configured to be the same as the width W1 or W2 of the respectively connected rectangular channels 4, or may be configured to be thinner than the width W1 or W2.

The particle trapping device 25 is provided with the rectangular channel 4 having a rectangular cross-section. The rectangular channel 4 may be configured in such a way that the target particles 6 in the liquid 20 that had flowed through the flattened channel 12 enter into the rectangular channel 4. The channel cross-section of the rectangular channel 4 is in the form of a cube or a rectangle. The rectangular channel 4 may also be shaped such that a corner or corners of the channel cross-section are rounded off. The rectangular channel 4 is configured in such a way that the inner wall face 8a and the inner wall face 8b are configured to be opposed to (or face with) each other, and the inner wall face 8c and the inner wall face 8d are configured to be opposed to (or face with) each other.

The particle trapping device 25 may be configured to be provided with the plurality of rectangular channels 4. This makes it possible to trap more target particles 6. For example, the particle trapping device 25 illustrated in FIGS. 1 to 3 is provided with four (4) rectangular channels 4.

In the particle trapping device 25, the rectangular channel 4 is provided with the particle pit trap 5 on the inner wall face 8a. The particle pit trap 5 disposed in this manner allows the target particle 6 flowing through the rectangular channel 4 to enter into the particle pit trap 5. The particle pit trap 5 may be shaped like a well.

The particle pit trap 5 may be configured to be 1.04 times or more to 3 times or less in size the average particle diameter S1 of the target particles 6. This makes it possible for the target particle 6 flowing through the rectangular channel 4 to enter into the particle pit trap 5; and this also makes it possible to inhibit the target particle 6 that had entered into the particle pit trap 5 from leaving the particle pit trap 5. The target particle 6 thus can be trapped (or captured) inside the particle pit trap 5. The particle pit trap 5 may be configured to be 1.1 times or more to 2.2 times or less in size the average particle diameter S1 of the target particles 6.

The particle pit trap 5 may be configured to have a depth D1 larger than the average particle diameter S1 of the target particles 6. The depth D1 of the particle pit trap 5 may be configured to be 1 time or more to 2.2 times or less the average particle diameter S1 of the target particles 6.

For example, in a case where the target particles 6 are 100 nm in average particle diameter S1, the particle pit trap 5 may be configured to be 110 nm or more to 300 nm or less in size; and the particle pit trap 5 may be configured to be 100 nm or more in depth D1. In a case where the target particles 6 are 1,000 nm in average particle diameter, the particle pit trap 5 may be configured to be 1,100 nm or more to 3,000 nm or less in size; and the particle pit trap 5 may be configured to be 1,000 nm or more in depth D1.

In a case where the particle pit trap 5 is in the form of a rectangle, a size of the particle pit trap 5 is determined by a length W4 or a length W5 of at least one side of the pit trap 5. In a case where the particle pit trap 5 is in the form of a circle, a size of the particle pit trap 5 is determined by a diameter or a long diameter W6 of the pit trap 5. Both the widths W4, W5 of the pit trap 5 may be configured to be 1.1 times or more to 3 times or less the average particle diameter S1 of the target particles 6.

The width W1 between the inner wall face 8a and the inner wall face 8b of the rectangular channel 4 is 1.04 times or more to 2.3 times or less the average particle diameter S1 of the target particles 6. This range makes it possible to increase probability of the target particle 6, which flow through the rectangular channel 4, entering into the particle pit trap 5. This was verified by experiments to be described below. In a case where the width W1 between the inner wall face 8a and the inner wall face 8b becomes larger than the above-mentioned range, it was found that the probability of the target particle 6, which flow through the rectangular channel 4, entering into the particle pit trap 5 decreases. Although it is uncertain why the above-mentioned range makes it possible to increase the probability of the entry of the target particle, it seems that the particle diameter of the target particle 6 is close to (or nearly the same as) the width of the rectangular channel 4.

By designing the W1 to be within the range mentioned above, it makes it possible to decrease the probability of the particle with a particle diameter less than the above-mentioned range of the particle diameter of the target particle 6 entering into the particle pit trap 5.

For example, in a case where the average particle diameter S1 of the target particles 6 is 100 nm, the width W1 between the inner wall face 8a and the inner wall face 8b may be configured to be 110 nm or more to 220 nm or less. In a case where the average particle diameter S1 of the target particles 6 is 1,000 nm, the width W1 between the inner wall face 8a and the inner wall face 8b may be configured to be 1,100 nm or more to 2,200 nm or less.

The width W2 between the inner wall face 8c and the inner wall face 8d of the rectangular channel 4 may be configured to be 1.04 times or more to 5 times or less the average particle diameter S1 of the target particles 6. This makes it possible for the target particles 6 to flow in a line through the rectangular channel 4, and also makes it possible to increase probability of the target particle 6 entering into the particle pit trap 5. For example, in a case where the target particles 6 are 100 nm in average particle diameter S1, the width W2 between the inner wall face 8c and the inner wall face 8d may be configured to be 110 nm or more to 500 nm or less. In a case where the target particles 6 are 1,000 nm in average particle diameter S1, the width W2 between the inner wall face 8c and the inner wall face 8d may be configured to be 1,100 nm or more to 5,000 nm or less.

By configuring the rectangular channel 4 to have the widths as described above, the target particles 6 forming a line flow together with the liquid 20 through the rectangular channel 4, as illustrated in FIG. 4(c) as an example. The target particle 6 flowing through the rectangular channel 4 enter into the particle pit trap 5 and is trapped therein, as illustrated in FIG. 4(d) as an example.

The rectangular channel 4 may be configured to have a plurality of particle pit traps 5 therealong that are placed at an appropriate interval. This enables many target particles 6 to be trapped in the pit traps. The plurality of adjacent particle pit traps 5 disposed on one rectangular channel 4 may be formed at regular intervals. This enables the particles 6 trapped in the pit traps 5 to be aligned, and makes it easy to observe and/or analyze the trapped particles 6. For example, the particle trapping device 25 illustrated in FIGS. 1 to 3 is provided with fourteen (14) particle pit traps 5 on one rectangular channel 4. The plurality of particle pit traps 5 disposed on the one rectangular channel 4 may be configured to have substantially a same size.

The inner wall face 8a having the particle pit trap 5 formed thereon may be the bottom of the groove disposed on the first substrate 2, or may be the side face of the groove disposed on the first substrate 2. In the case where the particle pit trap 5 is placed on the bottom of the groove disposed on the first substrate 2, the width between the inner wall face 8a and the inner wall face 8b becomes a width between the bottom of the groove disposed on the first substrate 2 and the inner wall face on the second substrate 3 side. In the case where the particle pit trap 5 is placed on the side face of the groove disposed on the first substrate 2, the width between the inner wall face 8a and the inner wall face 8b becomes a width between the side faces of the groove disposed on the first substrate 2.

The particle pit trap 5 may be in the form of a rectangle or may be in the form of a circle. The particle trapping device 25 illustrated in FIGS. 1 to 3 and FIG. 4(d) have the rectangular pit trap 5 disposed on the bottom of the groove of the first substrate 2. FIG. 5(a) illustrates the circular pit trap 5 disposed on the bottom of the groove of the first substrate 2. FIG. 5(b) and FIG. 6(b) illustrate the rectangular pit trap 5 disposed on the side face of the groove of the first substrate 2.

If the width of the channel is configured to be nano-sized or micro-sized, surface tension of the liquid becomes higher than gravity, with the result that the pit trap 5 allows the particle 6 to enter thereinto even if the pit trap 5 is disposed on the side face of the rectangular channel 4.

The particle pit trap 5 may be configured to trap one target particle 6. In this case, the depth D1 of the particle pit trap 5 may be configured to be 1 time or more to 1.5 times or less the average particle diameter S1 of the target particles 6. The particle pit trap 5 may also be configured to trap a plurality of target particles 6. In this case, the depth D1 of the particle pit trap 5 may be configured to be 2 times or more the average particle diameter S1 of the target particles 6. For example, FIGS. 1 to 3 illustrate the particle trapping device 25 having the particle pit trap 5 configured to trap one target particle 6. FIG. 6(a) illustrates the particle trapping device 25 having the particle pit trap 5 configured to trap two target particles 6.

The particle pit traps 5 may be disposed on different surfaces of the rectangular channel 4. For example, FIG. 6(c) illustrates the particle trapping device 25 having several particle pit traps 5 disposed on each of the opposed inner wall faces of the rectangular channel 4.

The particle pit trap 5 may be disposed in such a way that the target particle 6 can enter into the pit trap from the plurality of rectangular channels 4. For example, FIG. 6(d) illustrates the particle trapping device 25 having the particle pit trap 5 disposed in such a way that a rectangular channel 4a communicates with a rectangular channel 4b; and the target particle 6 flowing through the rectangular channel 4a and the target particle 6 flowing through the rectangular channel 4b may enter into the particle pit trap 5.

The particle trapping device 25 may be configured to have an auxiliary channel 21 and a connecting channel 22. The auxiliary channel 21 may be configured to extend substantially parallel to the rectangular channel 4. An end of the auxiliary channel 21 may connect with the exit-side channel 16. The connecting channel 22 may be disposed in such a way that the particle pit trap 5 communicates with the auxiliary channel 21. This enables the liquid 20 flowing through the rectangular channel 4 to enter into the particle pit trap 5, then to flow through the connecting channel 22 and the auxiliary channel 21, and then to flow into the exit-side channel 16, with the result that it makes it easy for the target particle 6 to enter into the particle pit trap 5. Also, by letting liquid or gas flow from the auxiliary channel 21 toward the particle pit trap 5, the target particles 6 trapped in the particle pit trap 5 can be collected.

The connecting channel 22 may be configured to have a channel cross-section that does not allow the target particle 6 to pass through the connecting channel. For example, the connecting channel 22 may be configured to have a width smaller than the average particle diameter of the target particles 6. This makes it possible to prevent the particle 6 that had entered from the rectangular channel 4 to the particle pit trap 5 from flowing to the auxiliary channel 21, with the result that the particle 6 can be trapped in the particle pit trap 5. This also allows the particles smaller than the target particles 6 out of the particles that had entered into the particle pit trap 5 to flow into the auxiliary channel 21, and makes it possible to inhibit the particles smaller than the target particles 6 from remaining (or staying) in the particle pit trap 5. The connecting channel 22 thus can be used for a filtering process.

For example, the particle trapping device 25 illustrated in FIG. 6(e) has the connecting channel 22 connecting a bottom of the particle pit trap 5 to the auxiliary channel 21.

The inner wall face 8b of the rectangular channel 4 may be disposed in such a way that the width between the inner wall face 8a and the inner wall face 8b varies. In this case, the width W1 may be designed as a width between the inner wall face 8a and the inner wall face 8b in the position of the particle pit trap 5. The inner wall face 8b of the rectangular channel 4 may be disposed in such a way that the width between the inner wall face 8a and the inner wall face 8b becomes narrow in the position of the particle pit trap 5, and may be disposed also in such a way that the width between the inner wall face 8a and the inner wall face 8b becomes wide between the two adjacent particle pit traps 5. This allows for the flow of the target particles 6 and the liquid through the rectangular channel 4 that makes the target particles 6 enter easily into the particle pit trap 5.

For example, the particle trapping device 25 may have the rectangular channel 4 as illustrated in FIG. 6(f).

The particle trapping device 25 may be provided with a first rectangular channel 4 for trapping first target particles 6 and a second rectangular channel 4 for trapping second target particles 6. The particle trapping device 25 may be provided with the different rectangular channels 4 for trapping the different target particles 6. Each of the rectangular channels 4 may be configured to have the widths W1, W2 accommodating the corresponding target particles 6. The particle pit traps 5 disposed on each rectangular channel 4 may be configured to have sizes accommodating the corresponding target particles 6. The rectangular channels 4 may be configured to accommodate the flattened channels 12, respectively. Each of the flattened channels 12 may be configured to have the thickness W3 accommodating the corresponding target particles 6.

The particle trapping device 25 as designed above is capable of allowing the particle pit traps 5 on the rectangular channels 4 to sort the particles 6 by their various particle diameter ranges and to trap the particles contained in the liquid 20 flowing through the lead-in channel 10.

For example, the particle trapping device 25 illustrated in FIG. 8 and FIG. 9 sorts four (4) target particles 6a to 6d. The target particles 6a to 6d have respectively different particle diameter ranges.

The particle trapping device 25 illustrated in FIG. 8 and FIG. 9 demonstrates as follows: a flattened channel 12a, a rectangular channel 4a, and particle pit traps 5a are configured to have a width and a size accommodating a target particles 6a; a flattened channel 12b, a rectangular channel 4b, and particle pit traps 5b are configured to have a width and a size accommodating a target particles 6b; a flattened channel 12c, a rectangular channel 4c, and particle pit traps 5c are configured to have a width and a size accommodating a target particles 6c; and a flattened channel 12d, a rectangular channel 4d, and a particle pit trap 5d are configured to have a width and a size accommodating a target particles 6d. FIGS. 8 and 9 illustrate that the rectangular channels 4 connect with the corresponding flattened channels 12, respectively; however, there may exist only one flattened channel 12; and the flattened channel 12 may be configured to have a thickness that changes in a stepwise fashion so as to accommodate each of the rectangular channels 4.

The particle trapping device 25 may be configured to have the exit-side channel 16. The exit-side channel 16 is to eject the liquid 20 that had already flowed through the rectangular channel 4. The exit-side channel 16 may be used to allow liquid to flow into the rectangular channel 4 after the particles 6 are trapped in the particle pit trap 5. To remove the liquid from the rectangular channel 4, gas such as air may flow through the exit-side channel 16.

The exit-side channel 16 may be configured in such a way that the liquid enters through an inlet port 18b, flows through the exit-side channel 16, and is ejected from an outlet port 19b. The exit-side channel 16 may also be configured in such a way that the liquid 20 that had flowed through the rectangular channel 4 flows to the exit-side channel 16.

The exit-side channel 16 may be disposed on the first substrate 2 or may be disposed on the second substrate 3; however, it is preferable that the exit-side channel is disposed on the second substrate 3. For example, the exit-side channel 16 may be placed in the particle trapping device 25 as illustrated in FIG. 1, FIG. 2 and FIG. 3(a).

When the particles 6-containing liquid 20 is supplied from the lead-in channel 10 to the rectangular channel 4, some of the particles 6 are trapped in the particle pit traps 5, and the rest of the particles 6 together with the liquid 20 enter into the exit-side channel 16. At this time the exit-side channel 16 does not have anything to flow through. When the liquid 20 is not supplied from the lead-in channel 10 to the rectangular channel 4, the rectangular channel 4 does not have anything to flow through. Following this, a cleaning liquid is supplied from the inlet port 18b to the exit-side channel 16; and then the cleaning liquid flows through the exit-side channel 16 and is discharged from the outlet port 19b. This enables the particles 6 and the liquid 20 that had entered into the exit-side channel 16 to be ejected from the particle trapping device 25. Part of the cleaning liquid flowing through the exit-side channel 16 enters into the rectangular channel 4 and then the flattened channel 12, and eventually enters into the lead-in channel 10. This enables the particles 6 and the liquid 20 remaining in the rectangular channel 4 and the flattened channel 12 to be discharged into the lead-in channel 10. At this time the target particles 6 trapped in the particle pit traps 5 are not discharged together with the liquid 20. In a case where particles having a smaller particle diameter than the target particles 6 are trapped in the particle pit traps 5, these particles may be discharged together with the cleaning liquid into the lead-in channel 10. By letting the cleaning liquid flow through the lead-in channel 10, the particles and the liquid 20 remaining in the lead-in channel 10 may be ejected from the particle trapping device 25.

This makes it possible to separate the target particles 6 from the particle 6-containing liquid 20 supplied to the lead-in channel 10, and to trap the target particles in the particle pit traps 5.

In the cases described above, the cleaning liquid flows from the exit-side channel 16 toward the lead-in channel 10 through the rectangular channel 4; however, the cleaning liquid may flow from the lead-in channel 10 toward the exit-side channel 16 through the rectangular channel 4.

In the following, how the target particles 6 trapped in the particle pit traps 5 are observed and analyzed will be described. Here are analyses of specific proteins present in a lipid bilayer membrane of exosomes (target particles 6).

Firstly, trap exosomes in particle pit trap 5 in the same way as above. Secondly, allow liquid containing primary antibodies to flow through the rectangular channel 4, and allow the primary antibodies to bond specifically with specific proteins (antigens) of the exosomes. Thirdly, allow a cleaning liquid to flow through the rectangular channel 4, and remove the extra primary antibodies, and then allow liquid containing secondary antibodies bonded to a fluorescent dye to flow through the rectangular channel 4, and allow the secondary antibodies to bond specifically with the primary antibodies. Then, allow a cleaning liquid to flow through the rectangular channel 4 and remove the extra secondary antibodies.

In this way the exosomes bonded to the fluorescent dye can be observed with a fluorescence microscope, and the specific proteins present in the lipid bilayer membrane of the exosomes can be analyzed.

The above is how to analyze the proteins of the lipid bilayer membrane; however, proteins, RNAs, lipids, etc. present inside the lipid bilayer membrane can be also analyzed.

Also, the particle trapping device 25 is capable of analyzing the exosomes one by one. The particle trapping device 25 is also capable of comprehensively analyzing exosomes secreted by one cell.

Another example of how to analyze target particles 6 is as follows. Allow liquid containing target particles 6 to flow into the rectangular channel 4, and allow the particle pit traps 5 to trap the target particles 6 therein. Then, allow water or a buffer solution to flow into the rectangular channel 4, and remove the untrapped target particles 6, etc. from the rectangular channel 4. Allow liquid that lyses target particles 6 to flow into the rectangular channel 4, and allow the liquid to lyse the target particles 6 trapped in the particle pit traps 5, and then collect the liquid containing the lysed target particles 6. By analyzing the collected liquid, the analyses of the target particles 6 can be obtained.

Another example of how to analyze target particles 6 is as follows. Allow liquid containing target particles 6 to flow into the rectangular channel 4 of the particle trapping device 25 as illustrated in FIG. 6(e), and allow the particle pit traps 5 to trap the target particles 6 therein. In this case, allow the liquid to flow in such a way that the liquid flowing through the rectangular channel 4 flows through the particle pit traps 5 and the connecting channel 22 and enters into the auxiliary channel 21. Then, allow water or a buffer solution to flow into the rectangular channel 4, and remove the untrapped target particles 6, etc. from the rectangular channel 4. By allowing the water or the buffer solution to flow through the auxiliary channel 21, then the connecting channel 22, and then the particle pit traps 5 and eventually to enter into the rectangular channel 4, the target particles 6 together with the water or the buffer solution can be taken into the rectangular channel 4 from the particle pit traps 5; and the target particles 6-containing water or buffer solution can be collected. By analyzing this target particles 6-containing water or buffer solution, the analyses of the target particles 6 can be obtained.

Another example of how to analyze target particles 6 is as follows. Allow liquid containing target particles 6 to flow into the rectangular channel 4 of the particle trapping device 25 on which a well-shaped particle pit traps 5 are disposed as illustrated in FIGS. 1 to 3 and FIGS. 6(a) to 6(c), and allow the particle pit traps 5 to trap the target particles 6 therein. Then, allow water or a buffer solution to flow into the rectangular channel 4, and remove the untrapped target particles 6, etc. from the rectangular channel 4. Then, allowing liquid capable of stimulating movement of the target particles 6 to flow into the rectangular channel 4, and taking the target particles 6 out of the particle pit traps 5 and into the rectangular channel 4, and collecting the target particles 6-containing liquid. The liquid capable of stimulating the movement of the target particles 6 may be liquid (such as a 1M KCl aqueous solution) capable of exerting an influence upon electrostatic interaction between the target particles 6 and an inner wall of the particle pit trap. By analyzing the collected target particles 6-containing liquid, the analyses of the target particles 6 can be obtained.

Experiments on Particle Trapping Devices Prepared

A particle trapping device (1), such as the one illustrated in FIGS. 1 to 3, was prepared. Used for a first substrate and a second substrate were quartz glass plates.

The first substrate was covered with an electron beam resist; and then parts of the electron beam resist (resist film) were removed by an electron beam, forming a resist pattern on the resist film. Then the resist film, as an etching mask, was subjected to etching; and a part of the first substrate was removed, forming a groove. By repeating such an etching process several times, grooves to become a flattened channel, a rectangular channel, a particle pit trap, etc. were formed on the first substrate. Also the second substrate was subjected to photolithography and an etching technique, forming grooves to become a lead-in channel and an exit-side channel. The first substrate and the second substrate were then washed and were allowed to come in contact with each other; and then these substrates were placed in a vacuum furnace and heated at 1,060° C., with the result that the first substrate and the second substrate were fused with each other. In this way the particle trapping device (1) was prepared, having the lead-in channel, the flattened channel, the rectangular channels, the particle pit traps, the exit-side channel, etc. disposed between the first substrate and the second substrate.

FIG. 10 shows a photograph and an SEM image of the particle trapping device (1) thereby prepared. FIG. 11(a) shows an SEM image of the first substrate used to prepare the particle trapping device (1), the first substrate having rectangular channels and particle pit traps formed thereon. The particle trapping device (1) was configured to have the particle pit traps formed on bottoms of the grooves disposed on the first substrate.

The flattened channel was configured to have a thickness W3 of 500 nm; the rectangular channel (nanochannel) was configured to have a width W1 of 500 nm; and the rectangular channel was configured to have a width W2 of 800 nm. The particle pit traps (nanowells) were configured to have sizes W4, W5 of 500 nm; and the particle pit traps were configured to have a depth D1 of 330 nm. Also, fifty (50) rectangular channels were formed; and one hundred and sixty (160) particle pit traps were formed on each of the rectangular channels.

FIG. 11(b), FIGS. 12(a) to 12(f), FIG. 13, and FIG. 14 show SEM images of the first substrate having particle pit traps formed on a side face of the grooves (rectangular channels) disposed on the first substrate. Also particle trapping devices were prepared, comprising the first substrate as shown in the SEM images of FIG. 11(b), FIGS. 12(a) to 12(f), FIG. 13, and FIG. 14. These particle trapping devices were prepared in the same way as the particle trapping device (1).

The particle trapping device provided with the first substrate as shown in the SEM images of FIG. 11(b), FIG. 12(a), and FIG. 14 has the particle pit traps formed on one side face of the rectangular channels, in a similar way to the particle trapping device 25 illustrated in FIG. 6(a). The particle trapping device provided with the first substrate as shown in the SEM images of FIGS. 12(b) to 12(e) has the particle pit traps formed on both side faces of the rectangular channels, in a similar way to the particle trapping device 25 illustrated in FIG. 6(c). The particle trapping device provided with the first substrate as shown in the SEM image of FIG. 12(f) has the rectangular channels whose width is designed to vary, in a similar way to the particle trapping device 25 illustrated in FIG. 6(f).

The particle trapping device provided with the first substrate as shown in the SEM image of FIG. 13 has the auxiliary channels and the connecting channels, in a similar way to the particle trapping device 25 illustrated in FIG. 6(e). This particle trapping device is configured to have thirty six (36) rectangular channels at intervals of 10 μm, each of the rectangular channels having a length of 400 μm, a width of 960 nm, and a depth of 350 nm. The device also is configured to have thirty six (36) auxiliary channels placed parallel to the rectangular channels, each of the auxiliary channels having a width of 510 nm and a depth of 350 nm. Each of the rectangular channels has one hundred and ten (110) particle pit traps at intervals of 5 μm, each of the pit traps being 680 nm×680 nm. The device is also configured to have connecting channels (neck structure) connecting the particle pit traps to the auxiliary channels, respectively, each of the connecting channels having a width of 350 nm.

A particle trapping device (2) comprising a first substrate, which is similar to the one shown in an SEM image of FIG. 14, was used for an experiment on trapped exosomes.

Experiment on Trapped Nanoparticles

Water containing fluorescent polystyrene particles (hereinafter referred to as PS particles) having an average particle diameter of 250 nm (concentration: $6.0 \times 10^9$ particles/ml) was dropped into an inlet port of the lead-in channel of the particle trapping device (1) prepared above; and the PS particles and the water flowed through the lead-in channel, the flattened channel, and the rectangular channels by capillary action. After that, water flowed through the rectangular channel; and the PS particles remaining in the rectangular channel were discharged from the particle trapping device. Then the PS particles trapped in the particle pit traps were observed with a fluorescence microscope. FIG. 15 shows an image taken with the fluorescence microscope; and white spots are the PS particles trapped in the particle pit traps. As is clear from FIG. 15, it was found that by allowing the PS particles-containing water to flow through the rectangular channels, the PS particles can be trapped in the particle pit traps.

Evaluations of Time Stability and Temperature Stability of Trapped Nanoparticles Water was kept on flowing through the rectangular channels of the particle trapping device (1) prepared above; and it was analyzed whether or not the PS particles trapped in the particle pit traps left the particle pit traps. More specifically, the water was kept on flowing through the rectangular channels for 24 hours; and then the PS particles trapped in the particle pit traps were observed with the fluorescence microscope. An upper photograph of FIG. 16 is an image taken with the fluorescence microscope showing the PS particles trapped in the particle pit traps before the water flowed through the rectangular channels; and a lower photograph of FIG. 16 is an image taken with the fluorescence microscope showing the PS particles trapped in the particle pit traps after the water was kept on flowing through the rectangular channels for 24 hours. It was found from the result thereby obtained that even though the water was kept on flowing through the rectangular channels for 24 hours, the PS particles leave the particle pit traps. It was also found from the other experiment that when the water did not flow through the rectangular channels, the PS particles did not leave (or did not escape from) the particle pit traps.

The PS particles trapped in the particle pit traps were also evaluated in terms of temperature stability. Even though the particle trapping device was heated to 100° C., the PS particles did not leave the particle pit traps.

This seems to be caused as follows: Once the PS particles are trapped inside the particle pit traps, interaction takes place between the PS particles and the wall faces of the particle pit traps (nanowells); and Brownian movement of the PS particles is inhibited, with the result that the PS particles are kept under restraint inside the particle pit traps.

It was found from these results that the plurality of nanoparticles can be stably arrayed for a prolonged time with accuracy of one particle.

Experiments on Trapped Mixed Nanoparticles

Experiments were carried out on red fluorescent polystyrene particles (hereinafter referred to as red PS particles) having an average particle diameter of 250 nm and green fluorescent polystyrene particles (hereinafter referred to as green PS particles) having an average particle diameter of 250 nm at the following mixing ratios, respectively: red PS particles:green PS particles=1:1, red PS particles:green PS particles=1:5, or red PS particles:green PS particles=1:10, the experiments being carried out to trap the red PS particles and the green PS particles in the particle pit traps. More specifically, water containing the red PS particles and the green PS particles (concentration: $6.0 \times 10^9$ particles/ml) at the above-mentioned mixing ratios was dropped into the inlet port of the lead-in channel of the particle trapping device (1) prepared above; and the red PS particles, the green PS particles, and the water flowed through the lead-in channel, the flattened channel, and the rectangular channels by capillary action. After that, water flowed through the rectangular channel; and the PS particles remaining in the rectangular channel were discharged from the particle trapping device. Then the red PS particles and the green PS particles trapped in the particle pit traps were observed with a fluorescence microscope; and ratios between the red PS particles and the green PS particles thereby detected were calculated. The calculated ratios are shown in FIG. 17. It was found from these results that the mixing ratios between the red PS particles and the green PS particles contained in the water injected into the particle trapping device were almost the same as the ratios between the red PS particles and the green PS particles detected. It was thus found that the particle trapping device prepared above can identify the mixing ratios of the nanoparticles contained in the liquid.

Measurements of Trap Rates of Nanoparticles

Seven (7) particle trapping devices were prepared, having respectively different widths W1 of the rectangular channel and thicknesses W3 of the flattened channel; and it was analyzed how the W1 and the W3 affected trap rates of the PS particles. The seven particle trapping devices prepared above were configured in such a way that the first substrate has a plurality of particle pit traps formed on one side face of the grooves of the first substrate, which is similar to the first substrate shown in FIG. 11(b), FIG. 12(a), and FIG. 14. The seven particle trapping devices prepared above were configured in such a way that a W2 is the same as the W3; and the widths W1 were designed to be 260 nm, 380 nm, 470 nm, 580 nm, 680 nm, 800 nm, and 900 nm, respectively. Other structures and a preparation method are the same as in the above-described experiments on the particle trapping devices prepared. Water containing fluorescent polystyrene particles (PS particles) having an average particle diameter of 250 nm flowed into the rectangular channel of the particle trapping devices; and then the PS particles trapped in the particle pit traps were observed with a fluorescence microscope. A trap rate was calculated for each of the particle trapping devices as follows: trap rate=(number of the detected PS particles)/(number of the particle pit traps in the particle trapping device). FIG. 18 shows the trap rates thereby calculated.

It was found that in the case where the width W1 of the rectangular channel was designed to be 580 nm (2.32 times the particle diameter of the PS particles) or more, the particle pit traps were not able to trap the PS particles therein. It was also found that in the case where the width W1 of the rectangular channel was designed to be 260 nm (1.04 times the particle diameter of the PS particles), the particle pit traps were able to trap the PS particles therein. It was also found that in the case where the width W1 of the rectangular channel was designed to be 380 nm (1.52 times the particle diameter of the PS particles), the trap rate of the PS particles was the highest.

As just described, it seemed that as the width W1 of the rectangular channel varied, the trap rate greatly changed. In the case where the W1 was small (or narrow), it seemed that the PS particles flowed along the inner wall of the rectangular channel, with the result that the PS particles were likely to enter into the particle pit traps easily, and the trap rate became high. It also seemed that in the case where the W1 was small, the PS particles carried electric charges, and the PS particles were likely to enter into the particle pit traps easily by electrostatic interaction. In the case where the W1 is too small, it seemed that the PS particles did not flow easily through the rectangular channel, leading to an increase in flow resistance and a decrease in trap rate. In the case where the W1 is too large, it seemed that the PS particles flowed easily through the rectangular channel, with the result that the flow resistance decreased; and the PS particles did not enter into the particle pit traps.

Experiments on Trapped Exosomes

Experiments on trapped exosomes were carried out with use of the particle trapping device (2) prepared above. The particle trapping device (2) was configured in such a way that a width of the rectangular channels was designed to be 410 nm, and a depth of the rectangular channels (i.e., a depth of the grooves of the first substrate) was designed to be 410 nm. A space between the two adjacent rectangular channels parallel to each other was designed to be 5 μm. A size of the particle pit traps (nanowells) was designed to be 320 nm×320 nm, and a depth thereof was designed to be 420 nm. A space between the two adjacent particle pit traps was designed to be 1.3 μm.

Human prostate cancer cells (PC-3 cells) in which green fluorescent proteins (GFP) were expressed were cultured in a culture medium; and then a culture supernatant was collected therefrom. This culture supernatant was filtered through a 0.2-μm filter. Exosomes contained in the filtered culture supernatant were measured for particle size distribution with use of a zeta potential/particle diameter measurement system. FIG. 19 shows measurement results thereby obtained. It was found that the culture supernatant contained the exosomes having a particle diameter of about 100 nm.

Next, the filtered culture supernatant was dropped into an inlet port of the particle trapping device (2) prepared above; and the culture supernatant flowed through the lead-in channel, the flattened channel, and the rectangular channels by capillary action; and then the exosomes were trapped in the particle pit traps. After that, water flowed to the rectangular channels; and the culture supernatant remaining in the rectangular channels was discharged from the particle trapping device (2). Then the rectangular channels and the particle pit traps were subjected to bright field observation and fluorescent observation. FIG. 20 shows bright field images, fluorescent images, and merged images thereof showing the rectangular channels and the particle pit traps. The bright field images of FIG. 20 show the rectangular channels and the particle pit traps as white lines extending transversely. It seems that luminous spots (circled to make it easy to locate) shown in the fluorescent images of FIG. 20 are the exosomes containing the GFP. As shown in the merged images of FIG. 20, it was confirmed that the exosomes were trapped in the particle pit traps.

By analyzing the exosomes trapped in the particle pit traps, the analyses of the exosomes can be obtained regarding RNA, proteins, and so forth present on surfaces of the exosomes and RNA, proteins, and so forth present inside the exosomes.

It was found that the particle trapping devices of the present invention were capable of trapping the exosomes in the particle pit traps and of analyzing the trapped exosomes in an effortless way.

REFERENCE SIGNS LIST

2: first substrate
3: second substrate
4, 4a, 4b, 4c, 4d: rectangular channel
5: particle pit trap
6: target particles
8, 8a, 8b, 8c, 8d: inner wall face
10: lead-in channel
12, 12a, 12b, 12c, 12d: flattened channel
14: cell trapping chamber
16: exit-side channel
18, 18a, 18b: inlet port
19, 19a, 19b: outlet port
20: liquid (dispersion medium)
21: auxiliary channel
22: connecting channel
24: cells
25: particle trapping device

What is claimed is:

1. A particle trapping device comprising: a lead-in channel; a flattened channel disposed on the downstream side of the lead-in channel; a rectangular channel disposed on the downstream side of the flattened channel; and a particle pit trap disposed at least on a first inner wall face of the rectangular channel, wherein the lead-in channel has a channel cross-section larger than a channel cross-section of the flattened channel and is configured whereby a liquid containing variously-sized particles including one or more target particles flows through the lead-in channel;

the flattened channel has a flat channel cross-section whose width is longer than its thickness;

the rectangular channel has a rectangular channel cross-section, and is provided with the first inner wall face, a second inner wall face opposed to the first inner wall face, a third inner wall face, and a fourth inner wall face opposed to the third inner wall face;

the particle pit trap is shaped like a well;

the lead-in channel, the flattened channel, the rectangular channel, and the particle pit trap are characterized by being configured in such a way that a portion of the liquid containing the one or more target particles and flowing through the lead-in channel flows into the flattened channel; the one or more target particles contained in the liquid that had flowed through the flattened channel flow into the rectangular channel; and the one or more target particles that had flowed through the rectangular channel enters into the particle pit trap and are trapped therein; and the width and the thickness of the flat channel cross-section are configured to allow the target particles to flow from the lead-in channel to the flattened channel and not to allow the particles larger than the thickness of the flat channel cross-section to flow from the lead-in channel to the flattened channel for filtering the liquid containing the one or more target particles.

2. The particle trapping device according to claim 1, further comprising a cell trapping chamber disposed between the flattened channel and the lead-in channel.

3. The particle trapping device according to claim 1, further comprising an exit-side channel; an auxiliary channel; and a connecting channel, wherein the exit-side channel is disposed on the downstream side of the rectangular channel;

the auxiliary channel extends substantially parallel to the rectangular channel, and one end of the auxiliary channel connects with the exit-side channel; and the connecting channel is configured to connect the particle pit trap to the auxiliary channel and is configured to have a channel cross-section that does not allow the one or more target particles to pass therethrough.

4. The particle trapping device according to claim 1, wherein the particle pit trap is one of a plurality of particle pit traps each characterized by being disposed on each of the first inner wall face and the second inner wall face.

5. The particle trapping device according to claim 1, wherein a width between the first inner wall face and the second inner wall face of the rectangular channel is 1.04 times or more to 2.3 times or less than an average particle diameter of the one or more target particles.

6. The particle trapping device according to claim 1, wherein a width between the third inner wall face and the fourth inner wall face of the rectangular channel is 1.04 times or more to 5 times or less than the average particle diameter of the one or more target particles.

7. The particle trapping device according to claim 1, wherein the particle pit trap has a size that is 1.04 times or more to 3 times or less than an average particle diameter of the one or more target particles.

8. The particle trapping device according to claim 1, wherein the particle pit trap is characterized by being larger than an average particle diameter of the one or more target particles.

9. The particle trapping device according to claim 1, wherein the flattened channel has a thickness that is 1.04 times or more to 2.3 times or less than an average particle diameter of the one or more target particles.

10. The particle trapping device according to claim 1, wherein the thickness of the flattened channel is configured to be substantially the same as a width between the first inner wall face and the second inner wall face or a width between the third inner wall face and the fourth inner wall face; and one of an upper plane and a lower plane of the flattened channel substantially lies in the same plane with the first inner wall face or the third inner wall face, and the other one of the upper plane and the lower plane substantially lies in the same plane with the second inner wall face or the fourth inner wall face.

11. The particle trapping device according to claim 1, comprising a first substrate and a second substrate; and wherein the rectangular channel has a structure in such a way that grooves formed on the first substrate are covered with the second substrate.

12. The particle trapping device according to claim 1, wherein the particle pit trap traps the one or more target particles therein.

13. The particle trapping device according to claim 1, wherein the one or more target particles are follicles, organelles, extracellular vesicles, viruses, liposomes, metallic particles, organic particles, inorganic particles, air pollution particulates, or pollens.

14. A particle trapping method characterized by comprising the steps of:

flowing liquid containing variously-sized particles including one or more target particles through a lead-in channel;

flowing a portion of the liquid containing the one or more target particles from the lead-in channel to a flattened channel;

flowing the liquid containing the one or more target particles from the flattened channel to a rectangular channel; and trapping at least one of the one or more target particles in a particle pit trap formed on a first inner wall face of the rectangular channel by entering into the particle pit trap, wherein the lead-in channel has a channel cross-section larger than a channel cross-section of the flattened channel;

the flattened channel has a flat channel cross-section whose the width is longer than its thickness;

the rectangular channel is provided with the first inner wall face, a second inner wall face opposed to the first inner wall face, a third inner wall face, and a fourth inner wall face opposed to the third inner wall face;

the particle pit is shaped like a well; and the width and the thickness of the flat channel cross-section are configured to allow the one or more target particles to flow from the lead-in channel to the flattened channel and not to allow a particle larger than the thickness of the flat channel cross-section to flow from the lead-in channel to the flattened channel.

15. The particle trapping method according to claim 14, wherein the flattened channel has the thickness that is 1.04 times or more to 2.3 times or less than an average particle diameter of the one or more target particles.

16. A particle trapping device comprising: a lead-in channel; a flattened channel disposed on the downstream side of the lead-in channel; a rectangular channel disposed on the downstream side of the flattened channel; and a particle pit trap disposed at least on a first inner wall face of the rectangular channel, wherein the lead-in channel has a channel cross-section larger than a channel cross-section of the flattened channel;

the flattened channel has a flat channel cross-section whose width is longer than its thickness;

the rectangular channel has a rectangular channel cross-section, and is provided with the first inner wall face, a second inner wall face opposed to the first inner wall face, a third inner wall face, and a fourth inner wall face opposed to the third inner wall face;

the particle pit is shaped like a well;

the lead-in channel, the flattened channel, the rectangular channel, and the particle pit trap are characterized by being configured in such a way that a portion of a liquid containing variously-sized particles including one or more target particles and flowing through the lead-in channel flows into the flattened channel; the one or more target particles contained in the liquid that had flowed through the flattened channel flow into the rectangular channel; and the one or more target particles that had flowed through the rectangular channel enters into the particle pit trap and is trapped therein; and the flattened channel has the thickness that is 1.04 times or more to 2.3 times or less than the average particle diameter of the one or more target particles.

* * * * *